(12) United States Patent
Perraudin

(10) Patent No.: US 9,115,211 B2
(45) Date of Patent: Aug. 25, 2015

(54) METHOD FOR PRODUCTION OF LACTOFERRIN

(76) Inventor: Jean-Paul Perraudin, Brussels (BE)

( * ) Notice: Subject to any disclaimer, the term of this patent is extended or adjusted under 35 U.S.C. 154(b) by 552 days.

(21) Appl. No.: 13/146,798

(22) PCT Filed: Jan. 28, 2010

(86) PCT No.: PCT/IB2010/000419
§ 371 (c)(1),
(2), (4) Date: Aug. 18, 2011

(87) PCT Pub. No.: WO2010/112988
PCT Pub. Date: Oct. 7, 2010

(65) Prior Publication Data
US 2011/0301077 A1   Dec. 8, 2011

Related U.S. Application Data

(60) Provisional application No. 61/202,088, filed on Jan. 28, 2009.

(51) Int. Cl.
| | |
|---|---|
| *A01N 37/18* | (2006.01) |
| *A61K 38/40* | (2006.01) |
| *A61K 47/48* | (2006.01) |
| *C07K 14/79* | (2006.01) |
| *C12N 5/00* | (2006.01) |
| *A61K 35/14* | (2006.01) |
| *C07K 1/00* | (2006.01) |
| *C07K 14/00* | (2006.01) |
| *C07K 16/00* | (2006.01) |
| *C07K 17/00* | (2006.01) |
| *A23J 1/20* | (2006.01) |
| *A23L 1/305* | (2006.01) |
| *A61K 38/00* | (2006.01) |

(52) U.S. Cl.
CPC . *C07K 14/79* (2013.01); *A23J 1/20* (2013.01); *A23L 1/3056* (2013.01); *A23V 2002/00* (2013.01); *A23V 2300/30* (2013.01); *A23V 2300/34* (2013.01); *A61K 38/00* (2013.01)

(58) Field of Classification Search
CPC ........... A23V 2002/00; A23V 2300/30; A23V 2300/34; A23V 2200/32; A23V 2250/54248; A23J 1/20; A23L 1/3056; A61K 38/00; C07K 14/79
See application file for complete search history.

(56) References Cited

U.S. PATENT DOCUMENTS

| | | | |
|---|---|---|---|
| 4,791,193 A | 12/1988 | Okonogi et al. | |
| 5,571,697 A * | 11/1996 | Conneely et al. | 435/69.7 |
| 5,976,597 A * | 11/1999 | Takada et al. | 426/491 |
| 6,096,870 A * | 8/2000 | Mozaffar et al. | 530/366 |
| 7,238,661 B2 * | 7/2007 | Glynn et al. | 424/145.1 |
| 2003/0096736 A1 * | 5/2003 | Kruzel et al. | 514/6 |
| 2004/0009895 A1 * | 1/2004 | Varadhachary et al. | 514/6 |

FOREIGN PATENT DOCUMENTS

| | | | | |
|---|---|---|---|---|
| EP | 0 730 868 A1 * | 9/1996 | ............. | A61K 38/40 |
| JP | A-2002-326950 | 11/2002 | | |
| JP | A-2008-214265 | 9/2008 | | |
| NZ | 221082 A | 1/1990 | | |
| WO | WO 2006/119644 A1 | 11/2006 | | |
| WO | WO 2009/009706 A1 | 1/2009 | | |

OTHER PUBLICATIONS

Adlerova et al. Lactoferrin: a review. Veterinarni Medicina, 2008. vol. 53, No. 9, pp. 457-468.*
Brock, Jeremy. The physiology of lactoferrin. Minireview. Biochem. Cell Biol. 2002, vol. 80, pp. 1-6.*
Tomita et al. Bovine lactoferrin and lactoferricin derived from milk: production and applications. Biochemistry and Cell Biology, 2002, vol. 80, No. 1, pp. 109-112.*
Yamauchi et al. Bovine lactoferrin: benefits and mechanism of action against infections. Biochemistry and Cell Biology, 2006. vol. 84, No. 3, pp. 291-296.*
Strydom et al., "An Angiogenic Protein from Bovine Serum and Milk Purification and Primary Structure of Angiogenin-2," *European Journal for Biochemistry*, 1997, pp. 535-544, vol. 247, Europe.
Naidu et al., "Influence of Lactoferrin on Host-Microbe Interactions," *Lactoferrin: Interactions and Biological Functions*, 1995, pp. 259-275, Humana Press Inc., Totowa, New Jersey, USA.
Naidu et al., "Specific Binding of Lactoferrin to *Escherichia coli* Isolated from Human Intestinal Infections," *APMIS*, 1991, pp. 1142-1150, Sweden.
Erdei et al., "Lactoferrin Binds to Porins OmpF and OmpC in *Escherichia coli*," *Infection and Immunity*, 1994, pp. 1236-1240, vol. 62, No. 4, American Society for Microbiology.

(Continued)

*Primary Examiner* — Marcela M Cordero Garcia

(74) *Attorney, Agent, or Firm* — Oliff PLC

(57) ABSTRACT

The invention concerns a method for production of lactoferrin comprising at least the steps of: a) disposing of raw material that have not been treated at a temperature greater than 500C, b) submitting this raw material to a treatment in order to obtain a solution of Lactenin (LN) or Milk Basic Protein (MBP), c) submitting this LN or MBP solution to a step of purification on a cation exchange resin equilibrated with an acetate buffer at a pH between 4 and 9 and eluted with different buffer solutions containing different solute concentrations, d) and collecting a fraction containing Lactoferrin having more than 95% of purity, having no polymers and substantially free of LPS, endotoxins and angiogenin. It also concerns the Lactoferrin obtained having more than 95% of purity, substantially free of LPS, endotoxins and angiogenin with an iron saturation level comprised between 9% to 15%.

19 Claims, 10 Drawing Sheets

(56) References Cited

OTHER PUBLICATIONS

Appelmelk et al., "Lactoferrin Is a Lipid A-Binding Protein," *Infection and Immunity*, 1994, pp. 2628-2632, American Society for Microbiology.
Elass-Rochard et al., "Lactoferrin-Lipopolysaccharide Interatction: Involvement of the 28-34 Loop Region of Human Lactoferrin in the High-Affinity Binding to *Escherichia coli* 055B5 Lipopolysaccharide," *Biochemistry Journal*, 1995, pp. 839-845, Great Britain.
Opal, "The Clinical Relevance of Endotoxin in Human Sepsis: A Critical Analysis," *Journal of Endotoxin Research*, 2002, pp. 473-476, vol. 8, No. 6, W.S. Maney & Son Ltd., USA.
Caccavo et al., "Review: Antimicrobial and Immunoregulatory Functions of Lactoferrin and its Potential Therapeutic Application," *Journal of Endotoxin Research*, 2002, pp. 403-417, vol. 8, No. 6, W.S. Maney & Son Ltd., USA.
Lee et al., "The Protective Effects of Lactoferrin Feeding against Endotoxin Lethal Shock in Germfree Piglets," *Infection and Immunity*, 1998, pp. 1421-1426, vol. 66, No. 4, American Society for Microbiology.
Yamauchi et al., "Effects of Orally Administered Bovine Lactoferrin on the Immune System of Healthy Volunteers," *Advances in Lactoferrin Research*, 1998, pp. 261-265, Plenum Press, New York, USA.
Hanson, "Biology of Human Milk," *Nestlè Nutrition Workshop Series*, 1998, vol. 15, Raven Press, New York, USA.
Nichols et al., "Iron is Not Required in the Lactoferrin Stimulation of Thymidine Incorporation into the DNA of Rat Crypt Enterocytes," *Pediatric Research*, 1990, pp. 525-528, vol. 27, No. 5, International Pediatric Research Foundation, Inc., USA.
Lönnerdal, "Trace Element Absorption in Infants as a Foundation to Setting Upper Limits for Trace Elements in Infant Formulas," *The Journal of Nutrition*, 1989, pp. 1839-1845, vol. 119, USA.
Cox et al., "Iron Binding Proteins and Influx of Iron Across the Duodenal Brush Border—Evidence for Specific Lactotransferrin Receptors in the Human Intestine," *Biochimica et Biophysica Acta*, 1979, pp. 120-128, vol. 588, Elsevier/North-Holland Biomedical Press.
Kawakami et al., "Isolation and Function of a Receptor for Human Lactoferrin in Human Fetal Intestinal Brush-Border Membranes," *American Journal of Physiology*, 1991, pp. G841-G846, American Physiological Society.
Rosa et al., "Iron Uptake from Lactoferrin by Intestinal Brush-Border Membrane Vesicles of Human Neonates," *Brazilian Journal of Medicial Biological Research*, 1994, pp. 1527-1531, vol. 27, No. 7, Brazil.
Shau et al., "Modulation of Natural Killer and Lympokine-Activated Killer Cell Cytotoxicity by Lactoferrin," *Journal of Leukocyte Biology*, 1992, pp. 343-349, vol. 51.
Miyazawa et al., "Lactoferrin-Lipopolysaccharide Interactions: Effect on Lactoferrin Binding to Monocyte/Macrophage-Differentiated Hl-60 Cells," *The Journal of Immunology*, 1991, pp. 723-729, vol. 146, No. 2, The American Association of Immunologists.
Erridge et al., "Structure and Function of Lipopolysaccharides," *Microbes and Infection*, 2002, pp. 837-851, vol. 4, Elsevier SAS.
Raetz et al., "Lipopolysaccharide Endotoxins," *Annual Revised Biochemistry*, 2002, pp. 635-700, vol. 71, National Institute of Health.
Majde, "Microbial Cell-Wall Contaminants in Peptides: A Potential Source of Physiological Artifacts," *Peptides*, 1993, pp. 629-632, vol. 14, Pergamon Press Ltd.
Rylander, "Endotoxin in the Environment—Exposure and Effects," *Journal of Endotoxin Research*, 2002, pp. 241-252, vol. 8, W.S. Maney & Son Ltd.
Tomita et al., "Bovine Lactoferrin and Lactoferricin Derived from Milk: Production and Applications," *Biochemistry Cell Biology*, 2002, pp. 109-112, vol. 80, NRC Canada.
Ulber et al., "Downstream Processing of Bovine Lactoferrin from Sweet Whey," *Acta Biotechnology*, 2001, pp. 27-34, vol. 21.
Zhang et al., "Isolation of Lactoferrin from Bovine Colostrum by SP-Sepharose Cation-Exchange Chromatography," 2002, pp. 614-617, vol. 57, Germany.
Machold et al., "Hydrophobic Interaction Chromatography of Proteins I. Comparison of Selectivity," *Journal of Chromatography A*, 2002, pp. 3-19, vol. 972, Elsevier Science B.V.
Ellison III et al., "Damage of the Outer Membrane of Enteric Gram-Negative Bacteria by Lactoferrin and Transferrin," *Infection and Immunity*, 1988, pp. 2774-2781, vol. 56, No. 11, American Society for Microbiology.
Ellison III et al., "Killing of Gram-Negative Bacteria by Lactoferrin and Lysozyme," *Journal of Clinical Investigation*, 1991, pp. 1080-1091, vol. 88, The American Society for Clinical Investigation, Inc.
Cohen et al., "Interaction of Lactoferrin and Lipopolysaccharide (LPS): Effects on the Antioxidant Property of Lactoferrin and the Ability of LPS to Prime Human Neutrophils for Enhanced Superoxide Formation," *The Journal of Infectious Diseases*, 1992, pp. 1375-1378, vol. 166, The University of Chicago, USA.
Zagulski et al., "Lactoferrin Can Protect Mice Against a Lethal Dose of *Escherichia coli* in Experimental Infection in Vivo," *Journal of Exp. Path*, 1989, pp. 697-704, vol. 70, Poland.
Berlutti et al., "Lactoferrin Downregulates Pro-Inflammatory Cytokines Upexpressed in Intestinal Epithelial Cells Infected with Invasive or Noninvasive *Escherichia coli* Strains," *Biochemistry Cell Biology*, 2006, pp. 351-357, vol. 84, NRC Canada.
Galand et al., "Cyclin/PCNA Immunostaining as an Alternative to Tritiated Thymidine Pulse Labelling for Marking S Phase Cells in Paraffin Sections from Animal and Human Tissues," *Cell Tissue Kinetics*, 1989, pp. 383-392, vol. 22, Belgium.
Harada et al., "Characteristic Transport of Lactoferrin from the Intestinal Lumen into the Bile via the Blood in Piglets," *Database Biosis* [Online] *Biosciences Information Service*, 1999, 1 page, XP002574410 Database accession No. PREV200000077344, Philadelphia, Pennsylvania, USA.
Hlroki et al., "Novel Angiogenic Disease-Treating Agents Containing Lactoferrins or Their Hydrolyzates," *CAPLUS*, 1997, 1 page, XP002967394.
Benzie et al., "Ferric Reducing/Antioxidant Power Assay: Direct Measure of Total Antioxidant Activity of Biological Fluids and Modified Version for Simultaneous Measurement of Total Antioxidant Power and Ascorbic Acid Concentration," *Methods in Enzymology*, 1999, pp. 15-27, vol. 299, Academic Press.
Law et al., "The Isolation and Bacteriostatic Properties of Lactoferrin from Bovine Milk Whey," *Journal of Dairy Research*, 1977, pp. 595-599, vol. 44, National Institute for Research in Dairying, Shinfield, Reading.
Yoshida et al., "Separation of Lactoferrin-a and -b from Bovine Colostrum," *Journal of Dairy Science*, 2000, pp. 2211-2215, vol. 83, Japan.
Naidu et al., "Lactoferrin Interaction with *Salmonellae* Potentiates Antibiotic Susceptibility in Vitro," *Diagn Microbiological Infectious Diseases*, 1994, pp. 64-75, vol. 20, Elsevier Science Inc., New York, USA.
Apr. 12, 2010 Written Opinion issued in International Patent Application No. PCT/IB2010/000149.
Apr. 12, 2010 International Search Report issued in International Patent Application No. PCT/IB2010/000149.

\* cited by examiner

METHOD FOR PRODUCTION OF LACTOFERRIN

FIELD OF THE INVENTION

The invention relates to the quality of the lactoferrin (Lf) to reach an optimal of all its activities and avoid any secondary effects

BACKGROUND OF THE INVENTION

Since its first identification as a "red protein" in bovine milk more than 65 years ago, and its purification in 1960, lactoferrin has intrigued and puzzled researchers. Subsequent determination of its amino acid sequence, three dimensional structure and detailed iron binding properties firmly established lactoferrin is a glycoprotein, as a member of the transferrin family, and reinforced the natural presumption that its biological function related to iron binding.

Different research centers have played an important role stressing on some biological key functions of the protein. Lactoferrin was isolated as a major component in the specific granules of the polymorphonuclear leukocytes with an important role in the amplification of the inflammatory response. Extensive work by Masson and its Belgian group has established a clear role for lactoferrin in cellular immunity and has led to the identification of specific lactoferrin-receptors on macrophages, intermediation of endotoxic shock and hyposideremia. Pioneering efforts by Montreuil and his French group unraveled the biological chemistry of lactoferrin. Lönnerdal has opened the nutritional role for lactoferrin in the absorption of metals ions in the intestinal tract. Broxmeyer and his co-workers reported a regulatory function for lactoferrin in myelopoiesis. From his side, Reiter reported the ability of milk lactoferrin to inhibit the growth of some microorganisms and found that nutritional deprivation of the bacteria from iron accounted for the antimicrobial activity. Arnold and his collaborators reported bactericidal activity for lactoferrin against a variety of microorganisms. Tomita and his research group at Morinaga Milk Industry in Japan has found that acid/pepsin hydrolysis of lactoferrin could generate cationic antimicrobial peptides "lactoferricin".

Several studies have established that lactoferrin supplementation could provide exceptional health benefits and a powerful protection against several illness. Functional characterization technologies have elucidated the molecular mechanisms of lactoferrin-mediated multifunctional activities. Furthermore, investigators from laboratories around the world have validated the functional outcomes with lactoferrin supplements in randomized human trials and in vivo experimental models.

But if the multifunctional activities of this extracellular glycoprotein that functions as a key component of the first line of mammalian immune defense against environmental insults have been demonstrated using a good quality of lactoferrin produced in the laboratory, we have discovered that it is not the case with the lactoferrin produced commercially.

During the industrial process, the Lf is extracted from milk or whey in presence of other Milk Basic Proteins (MBP) such as lactoperoxidase, some immunoglobulins and other contaminants of which the concentration is dependent of the specificity of the cationic ion exchange resin. It is an easy process that consists to extract and purify the Lf. In fact, we have the advantage that the most part of proteins and enzymes contained in the MBP are colored. The elution of the different components bound on the resin will be performed using solutions containing different NaCl concentrations. Using such procedures, the industrial producers consider that a purity between 90 to 92% correspond to a Lf enough pure to be used for the different applications.

However, none of these processes, nor any other existing process for commercial-scale purification of lactoferrin, are able to remove contaminants that affect the stability and activity of the lactoferrin.

It appears that contaminant enzymes are present in currently existing commercial lactoferrin preparation. These enzymes are co-purified during lactoferrin purification from milk or whey Regarding the contaminants, as it will be demonstrated below, we have also found that the angiogenin can be purified during the purification of the Lf. This molecule has a molecular weight of 15 kDa and an isoelectric pH of 9.5 very close to the Lf.

This molecule is responsible to the creation of the blood vessel to feed the cancer cells, neo-vascularization indispensable to the growth of tumors and to the development of the metastasis. During the purification of the Lf, this molecule has been concentrated at least 4 times what is certainly not beneficial for the health of the consumers.

Angiogenin contributes to an inflammatory process that allows the transmigration of endothelial and smooth muscle cells through basement membrane to enter a site of injury. Angiogenin promote the neovascular of the tumor cells and promote the proliferation of the metastasis of the cancer cells.

Angiogenin is a protein of 15 kDa with an isoelectric pH of 9.5 that means very close to Lf. As described by Strydom et al., in 1997 (Eur. J. Biochem, 247, 535-544, angiogenin was applied to a CM-52 (cation-exchange chromatography resin) and was eluted with 1M NaCl in 50 mM sodium phosphate, pH 6.6 solution. So it is not surprising that this molecule is co-purified with Lf and has been detected in the SDS-PAGE gel in presence of all the commercial Lf.

Another problem is the production by thermal treatment of Lf polymers that we have also demonstrated, see below.

Therefore, there is a great need for new purification and stabilization methods of lactoferrin preparations in order to remove contaminants, the protein degradation and the LPS to enhance, the activity on bacterial growth and to preserve the protein stability, for a longer period of time.

Although originally identified as an abundant protein in milk secretion, lactoferrin is expressed predominantly by surface epithelia and secreted into the mucosal environment. As described, lactoferrin is produced at high levels not only in the milk but also in nasal and tracheal passages and in gastric, genital, and ophthalmic secretions. Lactoferrin is also produced at high levels in neutrophils where it is stored in secondary granules and released during inflammation and contribute to their antimicrobial activity.

Lactoferrin contains 2 homologous iron binding domains that sequester available iron and can deprive iron-requiring domains bacteria of this essential growth element. In this manner, the protein exerts a bacteriostatic effect against a large range of microorganisms and certain yeast. Moreover, lactoferrin, by the presence of its cationic peptide located close to the amino-terminus of the protein, has shown to possess both bactericidal and anti-endotoxin activities that are independent of the iron binding function of the protein. This region acts by disrupting bacterial membranes and by binding and inactivating bacterial lipopolysaccharides containing the lipid-A called also endotoxins (see FIG. 1)

Lactoferrin is also able to regulate cellular signaling pathways, which affect activities such as its alleviation of inflammation, promotion of bone growth and suppression of carcinogenesis.

Thus its anti-inflammatory activity is linked to an ability to inhibit the production of pro-inflammatory cytokines, but by several distinct mechanisms, and its regulation of bone growth that occurs through mitogen-activated protein kinase pathways. Increasing number of studies show that lactoferrin possesses anti-cancer properties, inhibiting the growth of cancer, that stem from its ability to modulate pathways that impinge on the cell cycle or result in upregulation of the expression of cytokines as interleukin-18.

Moreover the antimicrobial functionality of lactoferrin is dependent on its protein conformational, metal binding and milieu conditions (Naidu A S and Arnold R R., 1995, Lactoferrin interactions and biological Functions pp 259-275 Totowa, N.J., Humana Press). Antimicrobial activity is enhanced when lactoferrin binds to the microbial surfaces. The specific lactoferrin binding microbial targets have been identified on different Gram-positive and Gram-negative bacterial pathogens (Naidu S S et al., 1991, APMIS, 99, 1142-1150). The high-affinity interaction of lactoferrin with pore-forming outer-membrane proteins of Gram-negative enteric bacteria including *Escherichia coli*, is critical for the antimicrobial outcome of lactoferrin (Erdei et al., 1994, Infect Immun, 62, 1236-1240). Thus, lactoferrin-mediated outer-membrane damage in Gram-negative bacteria and the lactoferrin-induced antibiotic potentiation by causing altered outer membrane permeation are typical examples of such antimicrobial outcomes (Naidu et al., Diagn Microbiol Infect, 1988, Infect Immun, 56, 2774-2781). Lactoferrin interaction with the microbial surface, the outer membranes in particular, has led to other antimicrobial mechanisms such as microbial adhesion-blockage to intestinal epithelia and specific detachment of pathogens from gut mucosa. Specific binding of lactoferrin could instantly collapse bacterial outer membrane barrier function and leads to the shutdown of pathogen colonization factors and enterotoxin production.

From another side, Appelmelk and his collaborators (Appelmelk B J, et al., 1994, Infection and Immunity, 62, 2628-2632) have found that Lf binds to the lipid A, part of the LPS and Elass Elass-Rochart E, et al., 1995, Biochem J. 312, 839-845) has demonstrated that this binding site is located in the N-terminal (peptide 1 to 52) of the lactoferrin where are also located the main part of the activities of the Lf. From these results, it is easy to understand the relation existing between the activity of the lactoferrin and the presence of the LPS bound on the molecular structure of the lactoferrin.

There is a continuous transfer of LPS and endotoxin from the intestinal lumen into the bloodstream. In healthy individuals, plasma inactivates the intestinal influx of LPS and endotoxin and protects internal organs from damage. However, any disturbances in gut permeability could increase LPS and endotoxin transfer into the bloodstream. Such massive influx could exhaust the ability of plasma to inactivate LPS and endotoxins and ultimately lead to clinical endotoxemia (Opal S M, 2002, J. Endotoxin Res, 8, 473-476). Experimental evidence suggest that reactive oxygen species are important mediators of cellular injury during endotoxomia, either as result of macromolecular damage or by interfering with extracellular and intracellular regulatory processes. An important mechanism to prevent physiological endotoxemia is to reduce lipopolysaccharides (LPS) from the intestinal lumen.

On its N-terminal (lactoferricin peptide) Lf binds to lipid-A, the toxic moiety of LPS with high affinity and works as a therapeutic agent to neutralize effects of LPS and endotoxins (Appelmelk B J et al, 1994, Infect Immun, 62, 2628-2632). Lf could effectively reduce LPS and endotoxin influx into the bloodstream while toxins still are inside the intestinal lumen but to reach such result, it is important that Lf is manufactured free of LPS and endotoxin. Moreover, if the Lf feeds by the healthy person is covered by LPS, these LPS could be removed from the molecule and be transferred into the bloodstream.

In this process, however, Lf is also depleted rapidly and may not be present in sufficient amounts to perform this function if LPS and endotoxins are continuously released in large quantities (Caccavo et al, 2002, J. Endotoxin Res, 8, 403-417). A protective effect for Lf against lethal shock induced by intravenously administered endotoxin has been reported. Lf-mediated protection against endotoxin (if the molecule is itself free of endotoxin during its production) challenge correlates with both-resistance to induction to hypothermia and an overall increase in wellness. In vitro studies with a flow cytometric measurement indicated that Lf inhibits endotoxin binding to monocytes in a dose-dependent manner, which suggests that the mechanism of Lf action in vivo could be due to the prevention of induction of monocyte/macrophage-derived inflammatory-toxic cytokines (Lee W J et al, 1998, Infect Immun, 66, 1421-1421).

Human clinical trials have also showed a positive influence of Lf consumption in primary activation of host defense (Yamauchi et al, 1998, Adv Exp Med Biol, 443, 261-265). Healthy people showed improvement in their serum neutrophil function including enhanced phagocytic activity and superoxide production. Furthermore, specific interaction of Lf with alveolar macrophages, monocytes, kupfer cells, liver endothelia, neutrophils, platelets, and T-lymphocytes emphasizes the role of Lf in mucosal and cellular immunity (Hanson L A, 1988, Biology of human milk. Nestlé Nutrition Workshop series, 15, New-York, Raven Press). Nevertheless, all this activity due to the interaction of the Lf with these cells is decreased by the presence of the LPS on the Lf structure and by the damages of the glycan chains of the Lf due to the use of the too high temperatures (>550° C. after 15 seconds) during the manufacturing process and due to the too high temperature for the drying of the molecule, and also by the presence of Lf polymers which appear during the heat treatment of the molecule.

Concerning gut maturation and mucosal repair it has been demonstrated that oral Lf administration could function as an immune stimulating factor in the intestinal mucosa.

The gastrointestinal tract matures more rapidly in the newborn during breast feeding. This activation is dependent on Lf binding to the intestinal epithelia. Lf could potentiate thymidine incorporation into crypt cell DNA in vivo. This trophic effect contributes to cell regeneration and tissue repair of intestinal mucosa in conditions such as gastroenteritis (Nichols et al., 1990, Pediatr Res., 27, 525-528). The presence of the LPS on the Lf structure decrease this activity of the Lf due to the fact that the Lf binding to the intestinal epithelia is located to the peptide (1-52) that means at the same place that the LPS Lf also plays an important role in the intestinal absorption of iron and other trace essential elements such as zinc, copper (Lonnerdäl B., 1989, J. Nutr. Suppl, 119, 1839-1844). Lf also protects the gut mucosa from excess uptake of heavy metal ions. Specific Lf binding receptors in the human duodenal brush border are involved in the iron absorption (Cox et al 1979, Biochem Biophy Acta, 588, 120-128). An intestinal Lf receptor was identified. Increased iron absorption via this Lf receptor from the intestinal brush-border membranes have been reported (Kawakami H et al., 1991, Am. J. Physiol, 261, G841-G846 and Rosa G et al., J. Med. Biol. Res, 27, 1527-1531) and here also the Lf peptide which is responsible to the binding of the molecule to its specific receptor has been localized on the peptide 1-52 which is also responsible to the binding of the LPS.

Concerning its anti-tumor activity, Lf is shown to enhance natural killer (NK) activity of monocytes in a dose-dependent manner. Lf strongly increases both NK and lymphokine-activated killer (LAK) cell cytotoxic functions. Lf is an effective modulator of cell-mediated immune response and serum cytotoxic factors at low dosages if the LPS are not bound on Lf structure and if Lf is not contaminated by the angiogenin. However, at higher concentrations the Lf-mediated induction could lead to a positive or negative feedback according not necessary to the density and subsets of the immune cell population but also to the presence of the LPS on the Lf structure.

Discovery of specific Lf receptors on macrophages, T and B-lymphocytes and leukemia cells establish the potential anti-tumor potential of Lf (Shau et al., 1992, L. Leukoc Biol, 51, 343-349) which could be eliminate by the presence of the LPS on its structure.

The anti-inflammatory activity of the Lf is primarily associated with its ability to scavenge iron. It is known that accumulation of iron in inflammed tissues could lead to catalytic production of highly toxic free radicals. During an inflammatory response, neutrophils migrate to the challenge site to release their Lf containing acidic granules. This results in the creation of a strong acidic milieu at the inflamed tissue site to amplify iron-sequestering and detoxification capacities of Lf. Besides modulating iron homeostasis during inflammation, there is mounting evidence that Lf could directly regulate various inflammatory responses. This iron-independent mode of action is based on Lf binding to bacterial LPS, which is major pro-inflammatory mediator during bacterial infections and septic shock (Miyazawa et al., 1991, J. Immunol, 146, 723-729). Lf could play an important role in the modulation of gastric inflammation, since this protein is also expressed in the gastric mucosa of the stomach and interacts with receptors localized on gastric intestinal epithelial cells. This activity of the Lf is completely decreased or even eliminated when LPS cover the Lf structure. Several in vivo studies have shown that oral administration of Lf could reduce gastric induced by *Helicobacter* pillory and protect gut mucosal integrity during endotoxemia. Here also such activity of the Lf is very poor when the LPS are bound on the Lf structure.

The iron-independent activity of the Lf can be described as follows: One of the central proinflammatory functions of endothelial cells is the recruitment of circulating leukocytes at inflammatory tissue sites. Lipolysaccharides (LPS) or endotoxins is a predominant glycolipid in the outer membrane of Gram negative bacteria. The LPS are potent stimulators of inflammation that induce either directly or through the intermediary of cytokines, the expression of adhesions molecules such as endothelial-leukocyte adhesion molecule (E-selectin) and intracellular adhesion molecule 'ICAM-1). Endotoxin stimulation of endothelial cells is mediated by soluble protein found CD14 (sCD14), a specific receptor. CD14 is a 55 kDa glycoprotein that exists in the serum and as an anchored protein (mCD14) on the surface of monocytes-macrophages. In this mechanism, depending of the concentration of the LPS (endotoxins), there is the presence of an intermediate called the LPS-binding protein (LBP), which catalyses the transfer of LPS monomers from aggregates to CD14 to form a sCD14-LPS complex. Thus, the activation of endothelial cells by the sCD14-LPS complex or by the LPS alone causes various pathophysiological reactions including fever and hypotension, promotes leukocytes infiltration and microvascular thrombosis and contributes, during septic shock, to the pathogenesis of disseminated intravascular inflammation.

Nevertheless, lactoferrin found in exocrine secretions of mammals and released from granules of neutrophils during inflammation is able to modulate the activation of the cells and avoid the severe damages causing by the presence of the LPS.

Following infection, lactoferrin concentrations, higher than 20 μgr/ml, can be detected in blood. Lactoferrin is part of a primary defense system against the inflammation. Any presence of bacteria in the organism, is going to induce the inflammation, cancer and other pathologies. This induction is going to stimulate immune responses including cytokine production, increase of expression of cell adhesion molecules, and pro-inflammatory mediator secretion by monocytes, macrophages and neutrophils, which are into specific host tissues by systemic LPS exposure. The response of the host to LPS is mediated by immune modulator molecules such as tumor necrosis factor alpha (TNF-alpha), members of the interleukins (IL) family, reactive oxygen species, and lipids. Overproduction of those mediators induces tissue damage that precedes multiple organ failure.

Lactoferrin prevents the LBP-mediated binding of LPS to mCD14 and decreases the release of cytokines from LPS-stimulated monocytes. Lactoferrin might also modulate the inflammatory process. Indeed, studies reported the protective function of lactoferrin against sublethal doses of LPS in mice. In conclusion, the ability of lactoferrin to bind free LPS may account, in part, for the anti-inflammatory activities of the molecule.

It is the reason why when the human and the animal take orally or by injection lactoferrin to reinforce or to avoid the deficiencies of its primary defense system, it is primordial that the quality of the lactoferrin is identical to the one which is produced from the endogen way in the healthy human who has to protect himself against the microbial invasions. Knowing that during the aging process, the endogenic lactoferrin production becomes very poor, obliging the patients to take exogenic lactoferrin either orally or by injection.

Contaminants in source material could compromise the human health applications of Lf. Several factors including the origin of source material, protein purification, drying process and harvesting methods, manufacturing environment and storage conditions, all cumulatively contribute to the bioburden of Lf protein. Accordingly, when used as a source material, milk, whey or milk serum could carry through fermentative streptococci (*Streptococcus thermophilus* . . . ) and a medium with an acidic environment could selectively enrich several yeast and molds. Incidentally, these microbial populations are commonly known to proliferate and competitively limit the growth of several probiotics.

Lf derived from milk with a contamination of the milk pool from mastitis source could introduce the presence of LPS from gram-positive cocci including *Streptococcus uberis, Staphycoccus aureus* and coagulate-negative staphylococci. On the other hand, environmental contaminants such as spore-forming *Bacillus* spp, *Acinetobacter calcoaceticus, Klebsiella oxytoca, Pseudomonas* spp, and coliform including *E. coli*. and the LPS of such microorganisms could gain entry into Lf material through elution buffer, biofouled equipment, air ducts, etc. . . . . Similar microbiological quality issues could exist for the GMO-derived and recombinant Lf proteins from various expression such as rice, tobacco, yeast, cell cultures or transgeninc animals. Therefore, elimination or significant reduction of such LPS microbial contaminants is highly desirable for human health applications of commercial Lf, in general.

As it is explained here above, the LPS and endotoxin content in the source material could adversely affect the Lf applications. The lipopolysaccharides (LPS) in the gram-negative bacterial outer membrane typically consist of a hydrophobic domain known as lipid-A (or endotoxin), a non-repeating core oligosaccharide, and a distal polysaccharide (or O-antigen) (Erridge et al., 2002, Microbes Infect, 4, 837-851). LPS and endotoxins could stimulate the induction of cytokines and other mediators of inflammation, which in turn could trigger a broad range of adverse physiological responses (Raetz et al., 2002, Annu Rev Biochem, 71, 635-700). Gram-negative bacterial bioburden of milk or its derivatives used in protein isolation, processing plant environment and conditions cumulative contribute to LPS and endotoxin levels in an Lf source material. It has been reviewed the potential reservoirs for endotoxin contamination during isolation of protein materials (Majde et al., 1993, Peptides 14, 629-632). Rylanders (Rylander 2002, J. Endotoxin Res, 8, 241-252) has also reviewed the occurrence of endotoxin level in different environmental conditions and further pointed out the risks associated with non-bacterial endotoxins, particularly 1-3-β-D-glucan from mold cell walls. Thus, the microbial keeping standards of chromatographic resins, sanitation practices of processing equipment even more significantly the water quality used in Lf purification, could cumulatively contribute to the LPS and endotoxin levels of the purified Lf material and thereby could limit in vivo applications of commercial Lf. Pre-existence of Lf-LPS and endotoxin complexes reduce the potential of Lf interaction with gut epithelia and diminish its ability to control intestinal influx of LPS and endotoxins.

Then, all the commercial lactoferrin should have to be devoided of LPS bound on its molecular structure. For example, Ward, Loren and col. in WO2009/009706 have described a method to remove the endotoxins bound to Lf and to produce endotoxin-free lactoferrin product (EFL). That is not the case if you analyze the LPS concentration using the *limulus* test. It has been also demonstrated that when this concentration of LPS bound on the lactoferrin structure is too important, the complex LPS-Lf is able to induce production of inflammatory mediators in macrophages to some extent, rather than inhibit totally LPS activity. It is mainly due to the fact that when the LPS concentration is too important, there is an equilibrium between LPS bound→LPS-free and it is the presence of the LPS-free which induce production of inflammatory mediators. For safety, reasons that oblige the Lf producers to purify the molecule exempt of LPS bound on the surface of the Lf molecular structure.

Manufactured from the milk and/or the whey, it is normal that the lactoferrin is covered on its molecular structure by the bacterial LPS existing in the milk and that can be dangerous if such milk pool has been contaminated by microbial contaminated milk responsible of mastitis cows. We know that a part of the lactoferrin activities is represented by its antibactericidal role binding to the LPS of the bacteria existing in the milk. That means it is not surprising to extract from the milk a lactoferrin fully covered by LPS which has lost an important part of its biological activity regarding the antioxidant, the antibacterial and its activity to inhibit the bacterial biofilm formation and its prebiotic activity respectively.

Moreover Lf could be denaturized by heat treatment. There are different parameters that can be used to study the thermal stability of the lactoferrin. The heat treatment denaturation follows a first order kinetic. The denaturation increases with the temperature. The iron-free lactoferrin (Apo-Lactoferrin) shows a more rapid denaturation than the iron-saturated lactoferrin (Holo-Lactoferrin). That reflects to a more stable conformation when it is bound to iron. During thermal denaturation, the break of several binding provokes important changes in the Lf structure. The thermal stability is increasing in presence of other milk components due to the interaction between the lactoferrin and caseinates and other milk proteins.

The lactoferrin that is extracted from milk has an iron saturation level between 9 to 20% of the iron-saturated lactoferrin. However, after pasteurization of the milk or cheese whey, the protein which is extracted, has not the same activity level and not the same values compared to the lactoferrin, which has been extracted before any heat treatment of the milk or the cheese whey In fact, the heat treatment is able to destroy the glycan chains of the molecule which are important to protect the lactoferrin against proteolytic enzymes that are present in the stomach and is also able to produced Lf polymers. This effect has been also demonstrated by the fact that when lactoferrin is submitted to a heat treatment, the molecule has a higher absorbance power at 280 nm (Table 1).

The destroying of the glycan chains, which are sensitive to the heat treatment will also increase the non-specific binding of the lactoferrin on the cells. Instead to promote the cell growth, the non-specific binding of the lactoferrin will rather induce the suffocation of the cells. Actually, it has been established by the producers of commercial Lf that the purity of Lf is determined by Reverse Phase HPLC using an acetonitril gradient. Analysing the purity of some commercial Lf, we observe that the proteic contaminants represent around 8 to 9% versus the Lf peak. Nevertheless, diluting the same amount of commercial Lf, adjusted by the ash and moisture content, we have not found the same optical density at 280 nm. That means that some proteins eluting as Lf can increase the optical density. In the FIG. 2 , , , we can observe that Lf analyzed by ion-exchange chromatography FPLC (Mono-S resin-Sulfopropyl) show a smaller surface compared to the heat-treatment Lf surface. The reduction of the height of the surface is due to the presence of a new surface which corresponds to the shoulder observed with the FPLC analysis and that we call peak C to simplify the description of the chromatogram. We could also observe that the Lf surface is split into two parts: peak A and peak B very closed each other and corresponding for the peak A to the presence of one sialic acid content which give to the molecule a less basic behavior compared to the native one which does not contain sialic acid In case of the Lf-NFQ, the Lf surface is also composed of two surfaces (surface A and surface B). The shoulder (surface C) is only observed in the commercial Lf. The shoulder or surface C has a higher absorbance power at 280 nm compared to the native Lf see Table 1 below.

Anyway, we can consider that the peak A and peak B are parts of the pure Lf. The presence of the peak C cannot be detected with the use of the Reverse Phase chromatography. To understand the presence of this peak C, we have carried out the complete absorbance spectra from 280 nm to 800 nm and we have observed a band of Soret at 410 nm (FIG. 2) which is independent of the iron content in the Lf because this band of Soret should have to be present at a wavelength closed to the 465 nm. Moreover, the absorbance of this peak C at 280 nm is almost double to the Lf one.

Collecting only the peaks A and B, and applying again on the Mono S resin, we can notice that only the peaks A and B are present in the chromatogram without to be contaminated by the peak C. On the other hand, if we submitted the solution containing the peaks A and B to a temperature of 72° C. during 5 minutes and that we analyze this solution on the Mono S resin, we observe an important decrease of the surface of the peak A and of the surface of the peak B compared to the original chromatogram but also an appearance of the peak C (FIG. 2). More long time, we submit Lf to a heat treatment, more the peaks A and B will have a lower surface and more the peak C will be important.

If we compare on the Reverse Phase, the chromatogram of the Lf without heat treatment and the chromatogram of the same Lf but which has been submitted to a heat treatment (72° C.) during 5 min, we can notice that the surface of the Lf without heat treatment is lower that the surface of Lf having submitted a heat treatment (FIG. 3). The peak C has been characterized as Lf polymers having a much higher absorption power.

TABLE 1

| Heating (30 seconds) | Absorbance at 280 nm for a Lf solution of 1 mg/ml |
|---|---|
| <50° C. | 1.326 |
| 70° C. | 1.38 |
| 80° C. | 1.42 |
| 85° C. | 1.42 |

The problem is not only based on the fact that the lactoferrin purified by the manufacturer has lost a percentage of its biological activities what could be compensate by the adding of an higher concentration of the molecule but by the fact than more we advise the use of a high Lf concentration to reach a certain level of activity, more we recommend the use of a high LPS concentration. That could automatically induce the inflammatory process instead to protect the patients (Table 3).

Several Lf products are currently available in the health food markets worldwide. A majority of such products are derived from partially isolated Lf from colostrums, milk or cheese whey. Furthermore, the microbiological and toxicological quality issues compromise the in vivo performance standards of Lf as a potent food material.

Lactoferrin is usually purified from milk or whey (milk whey or cheese whey) by one or more different types of chromatography resins such as ion exchange, especially cation-exchange, affinity (immobilized heparin, single strand DNA, lysine or arginine) dye affinity and size exclusion. Ultrafiltration membrane can also be used to separate lactoferrin from milk or whey. Tomita and his collaborators (Tomita et al., 2002, biochem Cell Biol, 80, 109-112) have given an example of the industrial process which uses both cation-exchange chromatography and tangential-flow membrane filtration. Other purification using cation-exchange chromatographies have been described by Okonogi and his co-workers (Okonoki et al., New Zealand Patent N° 221,082), by Ulber (Ulber et al., 2001, Acta Biotechnol, 21, 27-34) and Zhang and his co-workers (Zhang et al., Milchwissenschaft 2002, 57, 614-617). Some researchers have used the hydrophobic properties of the molecule to purify the lactoferrin using hydrophobic interaction chromatography. Machold has described the retention behavior of lactoferrin on several hydrophobic interaction resins under range of salts concentrations (Machold et al, 2002, J. Chromatogr. A972, 3-19).

Different methods have been largely described by Dr Denis Petitclercq in the patent application WO 2006/119644 and the aim of his invention was to provide a process to remove enzyme contaminant responsible for lactoferrin degradation. The removal of these enzymes or addition of specific inhibitors would prevent degradation of a lactoferrin preparation and loss of activity of lactoferrin. He has applied his process to all commercial lactoferrin demonstrating that it is possible to improve the stability and the activity of the lactoferrin. He provides a method for purifying lactoferrin comprising the steps of contacting in a bind-and-elute mode and in an adsorptive fashion a solution of lactoferrin, with a hydrophilic absorbent and with a hydrophobic with the presence of surfactant, both in the presence of an excluded solute, and collecting a fraction containing lactoferrin substantially free of contaminant enzyme and/or lactoferrin inhibitor.

He has demonstrated that compared to the purified lactoferrin using its methods, the commercial lactoferrin manufactured from the same supplier as well as other suppliers available on the market did not display the same activity. In regards with the antibacterial activity, the purified lactoferrin did not lose its activity at higher concentration of lactoferrin in the medium (FIG. 4). None of the commercial lactoferrin preparations available on the market were able to display a minimum inhibition concentration and he has demonstrated that these commercial lactoferrin extracted from milk or whey have lost its, growth inhibitory activity at high concentration. Nevertheless, Dr Petitclerc has concluded that such phenomenon was due to the presence of proteases or degraded peptides Lf but he has never mentioned the presence of angiogenin.

Despite all the studies, none of the industrial processes, nor any other existing process for commercial scale purification, are able to purify the lactoferrin as it is present in our different secretion liquids.

SUMMARY OF THE INVENTION

It is an object of the invention to circumvent these issues and Lf of the same quality as it is produced in the organism, avoiding the presence of contaminants such as proteolytic enzymes and the angiogenin, avoiding the presence of the bacterial lipopolysaccharides (including the endotoxins), avoiding the destruction of the glycan chains and the appearance of Lf polymers by any heat treatments using a temperature above 55° C. has been developed using a novel technology which allows to produce commercially such a Lf which is able to have at least 90% of its biological activities.

It is an object of the invention to provide a process that permits:
 to remove effectively contaminants that affect the stability and the activity of lactoferrin and to remove contaminants having a negative effect of the health.
 to take care about the heat sensibility of the glycan chains that are responsible to protect the molecule against the proteolytic degradation of the proteases, also important to improve the binding of the molecule on certain cells and to avoid the appearance of Lf polymers.
 to remove the presence of the bacterial LPS and endotoxins bound on the molecular structure of the lactoferrin that affects the activity of the molecule but also can induce by their presence the inflammation process.

In accordance with the present invention there is provided a method for production of lactoferrin comprising at least the steps of:
 a) disposing of raw material that have not been treated at a temperature greater than 55° C.,
 b) submitting this raw material to a treatment in order to obtain a solution of Lactenin (LN) or Milk Basic Protein (MBP),
 c) submitting this LN or MBP solution to a step of purification on a cation exchange resin equilibrated with an acetate buffer at a pH between 4 and 9 and eluted with different buffer solutions containing different solute concentrations, d) and collecting a fraction containing Lactoferrin having more than 95% of purity, substantially free of LPS, endotoxins and angiogenin.

In one embodiment the step b) is a step of submitting this raw material to a step of extraction on a cation exchange resin using an excluded solute concentration solution in order to obtain a solution of Lactenin (LN), (FIG. 5a)

In an embodiment the steps of extraction or purification on a cation exchange resin are done in flow through or bind and elute mode.

In an embodiment the excluded solute is sodium chloride. In another embodiment a step of concentration and diafiltration is done after the step b).

In a further embodiment the step c) comprises at least four steps of elution, a step to collect the contaminants, a step to collect the Lactoperoxidase, a step to collect LPS, endotoxins and angiogenin and a step to collect the Lactoferrin (FIG. 5b).

In an embodiment the steps to collect the contaminants, the Lactoperoxidase, the LPS, the endotoxins and the angiogenin are performed at a pH between 4 and 8, and preferably between 6 and 7.

In an embodiment the steps to collect the Lactoferrin is performed at a pH comprised between 7 and 9.

In an embodiment in the purification step the solute is sodium chloride at a concentration comprised between 0.02 to 1.5 M.

In accordance with the present invention there is provided a Lactoferrin having more than 95% of purity, substantially free of LPS and endotoxins and with an iron saturation between 9 to 20%.

In a further embodiment the Lactoferrin comprises less than 50 pg/mg of LPS, endotoxins and angiogenin.

In a further embodiment the Lactoferrin has an iron saturation level is comprised between 9% to 20%.

DETAILED DESCRIPTION OF THE PREFERRED EMBODIMENTS

Since Lf is denatured by heat treatment depending on the conditions, pasteurized raw materials such as bovine colostrums, bovine milk and cheese whey are not suitable as a source for bLf (bovine lactoferrin) purification. Therefore, skim milk, cheese whey and colostrums that have not undergone rigorous heating can be sources of bLf. Because Lf has a cationic nature according to its amino acid composition, it can be purified by cation-exchange chromatography such carboxymethyl (CM)-Sephadex (Law et al., 1977; Yoshida et al., 2000) and this purification method is the most popular procedure for bLf purification in bLf-supplying companies. For example, skim milk (pH 6.7) or cheese-whey (pH 6.4) is filtered and applied to a cation-exchange chromatography column without pH adjustment.

Figure 1:
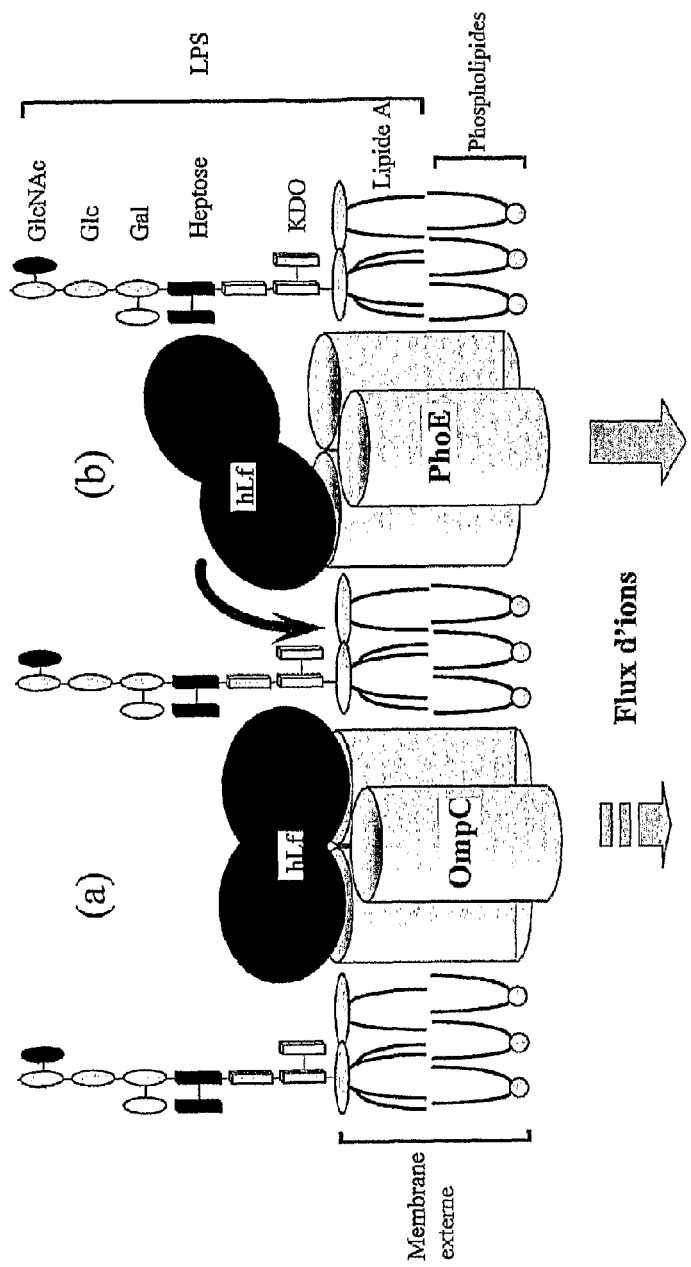
FIG. 1 illustrates the localization of the LPS and lipid A (endotoxin) on the cell wall of Gram negative bacteria
Figure 2:
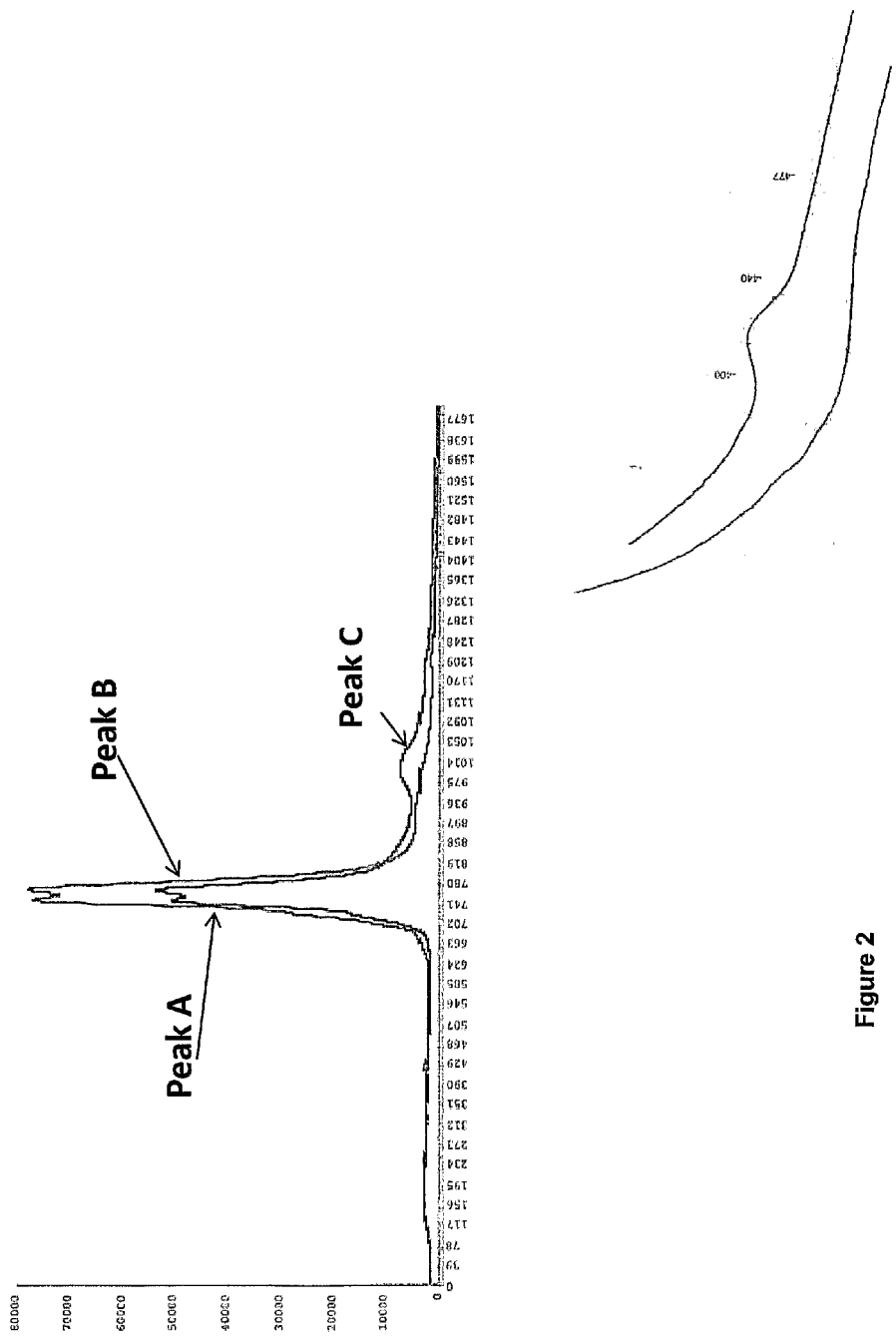
FIG. 2, illustrates the chromatogram on ion-exchange FPLC chromatography of the Lf (green) which has not been submitted to a heat treatment and the chromatogram of the same Lf which has been submitted to a heat treatment (red).
Figure 3:
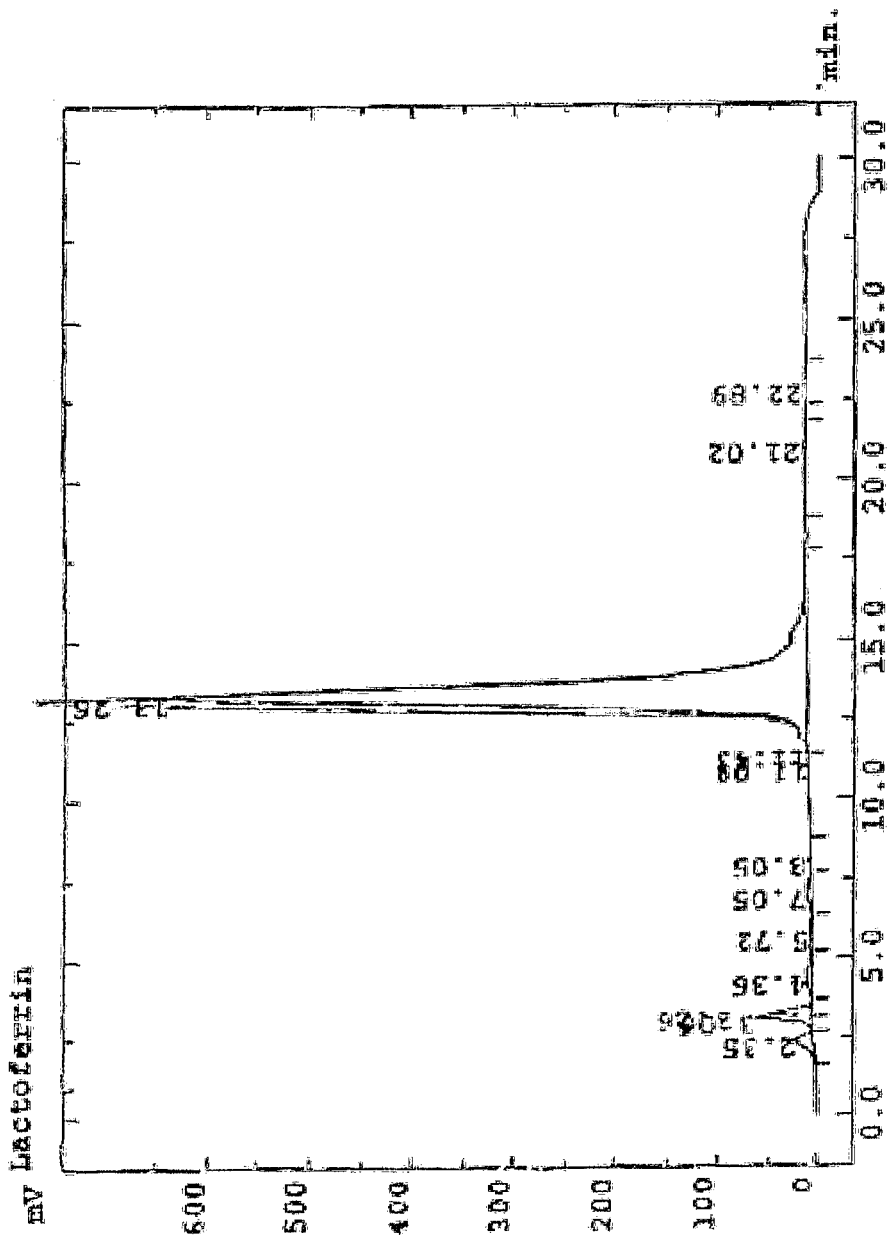
FIG. 3, illustrates the chromatogram on Reverse phase HPLC with a Lf which has not been submitted to a heat treatment and the same Lf which has been submitted to a heat treatment.
Figure 4:
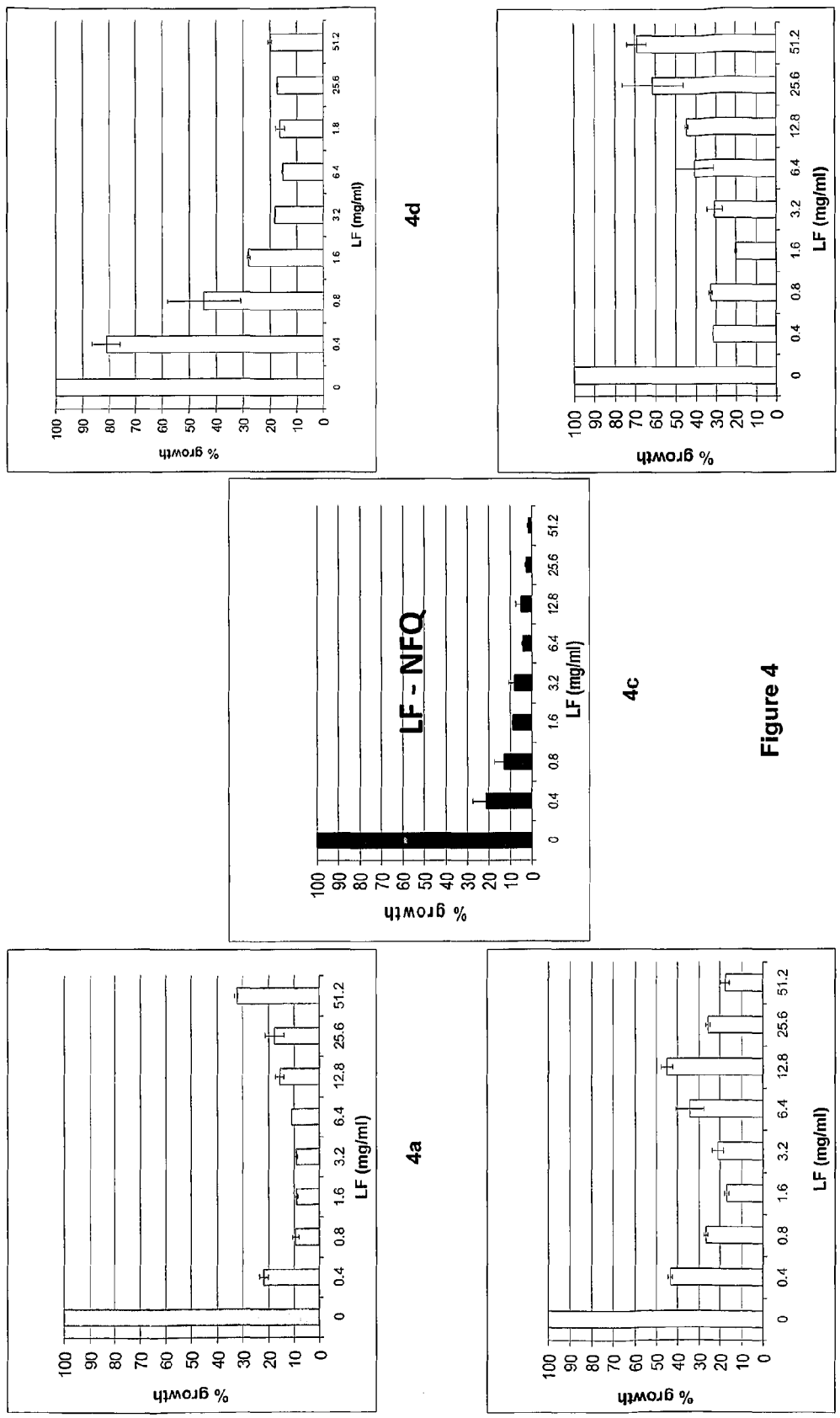
FIG. 4: Illustrates the determination of the Minimal inhibitory concentrations (MIC) using broth microdilution of bovine Lf purified on SP-Sepharose Fast Flow called Lf-NFQ compared to different commercial Lf preparations.
Figure 5:
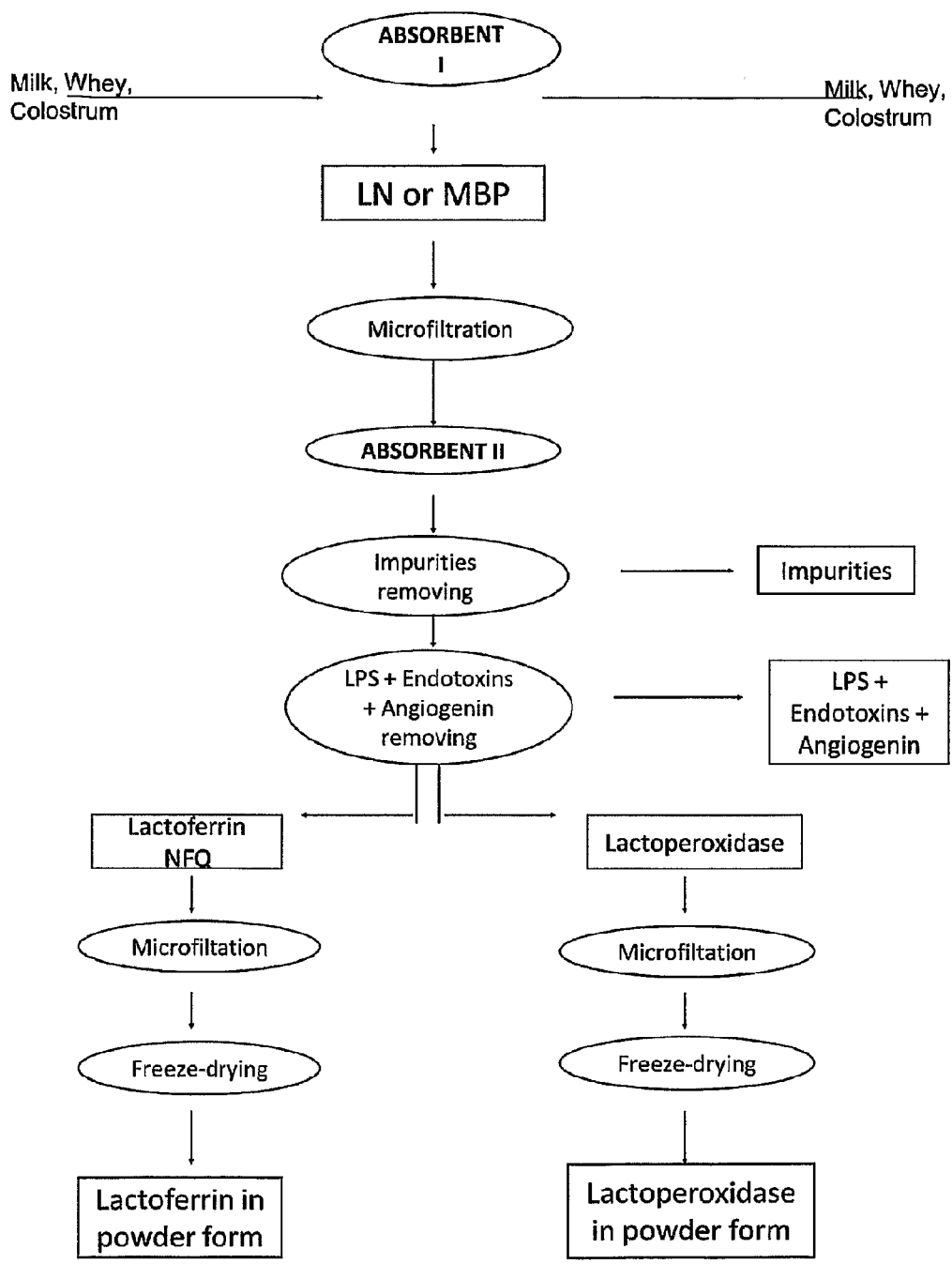
FIG. 5: Illustrates a flow chart of the production of Lactoperoxidase and lactoferrin FIG. 6. Illustrates the general diagram of the Lf purification.

As described in the FIG. 5, the material which will be eluded from a cation-exchange resin (Extraction resin) using a high NaCl concentration solution (8%), is called Lactenin (LN) or Milk Basic Protein (MBP). The LN is a solution containing Lactoferrin, Lactoperoxidase and some other molecules (+/−5%).

Figure 6:
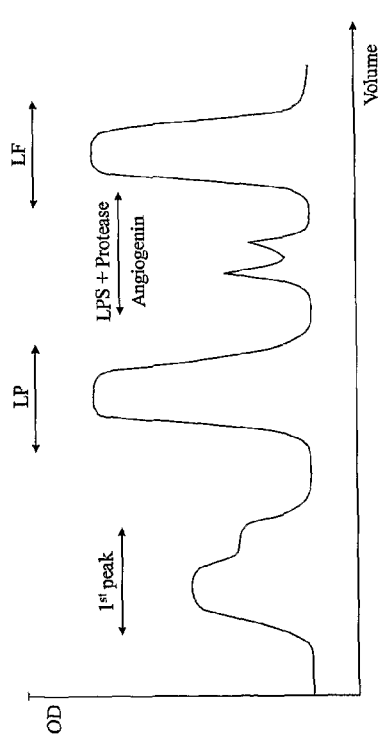

This LN will be microfiltrated, concentrated and diafiltrated before to be applied to another cation-exchange resin equilibrated with an acetate buffer at pH 5.5 and that we called the Purification Resin. In fact, during this second chromatography, the different molecules contained in the LN will be eluted by applications of different buffer solution containing different NaCl concentrations. This second chromatography is very important to obtain a lactoferrin as claimed. (FIG. 6)

The lactoferrin is concentrated by ultrafiltration and is separated from NaCl by diafiltration. Afterwards, the Lf solution will be dried at low temperature and under vacuum (freeze-dry technology) and stocked in food grade aluminium sachets.

The lactoferrin obtained by the claimed process is in the following description called Lf-NFQ Thermal and Chemical Stability of Lactoferrin There are different parameters that can be used to study the thermal stability of the lactoferrin. The heat treatment denaturation follows a first order kinetic. The denaturation increases with the temperature. The iron-free lactoferrin (Apo-Lactoferrin) shows a more rapid denaturation than the iron-saturated lactoferrin (Holo-Lactoferrin). That reflects to a more stable conformation when it is bound to iron. During thermal denaturation, the break of several binding provokes important changes in the Lf structure. The thermal stability is increasing in presence of other milk components due to the interaction between the lactoferrin and caseinates and other milk proteins.

The lactoferrin that is extracted from milk has an iron saturation level between 9 to 20% of the iron-saturated lactoferrin. However, after pasteurization of the milk or cheese whey, the protein which is extracted, has not the same activity level and not the same values compared to the lactoferrin, which has been extracted before any heat treatment of the milk or the cheese whey.

In fact, the heat treatment is able to destroy the glycan chains of the molecule which are important to protect the lactoferrin against proteolytic enzymes that are present in the stomach and to produce Lf polymers. This effect has been also demonstrated by the fact that when lactoferrin is submitted to a heat treatment, the molecule has a higher absorbance power at 280 nm.

Iron Binding Activity of the Lactoferrin

The activity of the lactoferrin extracted from microfiltrated milk has been tested for its iron binding activity. Lactoferrin is gradually brought to complete saturation by successive addition of aliquots of a ferric iron solution. The rate of iron saturation is followed spectrophotometrically at 465 nm.

Figure 7:
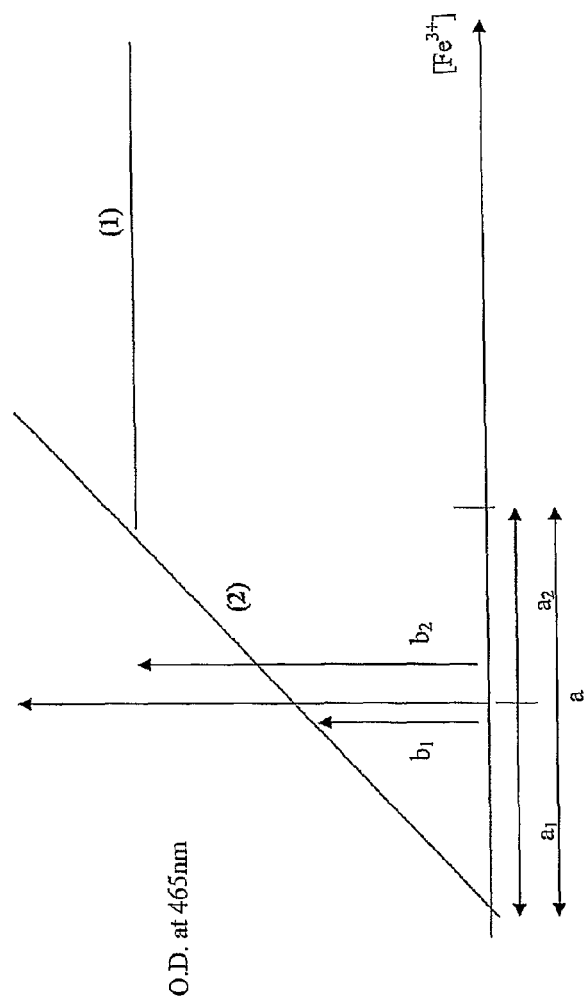
FIG. 7 illustrates the measure of the iron-binding capacity by an optical density of the Lactoferrin gradually brought to complete saturation by successive addition of aliquots of a ferric iron solution.

Saturation is achieved when the measure optical density no longer varies (FIG. 7). In the graphic, there are two ways to evaluate the initial rate of iron saturation in calculating the ratio of absorbance measured at 465 nm for the native protein (b1) and the saturated protein (b2).

$$b1 \text{ - - - } \times 100 = \% \text{ initial saturation} b2$$

or by calculating a1/a where
a1:=µmoles of ferric ions bound to the native protein
a=µmoles of ferric iron bound to the saturated protein $$a1 \text{ - - - } \times 100 = \% \text{ initial saturation}$$

Figure 8:
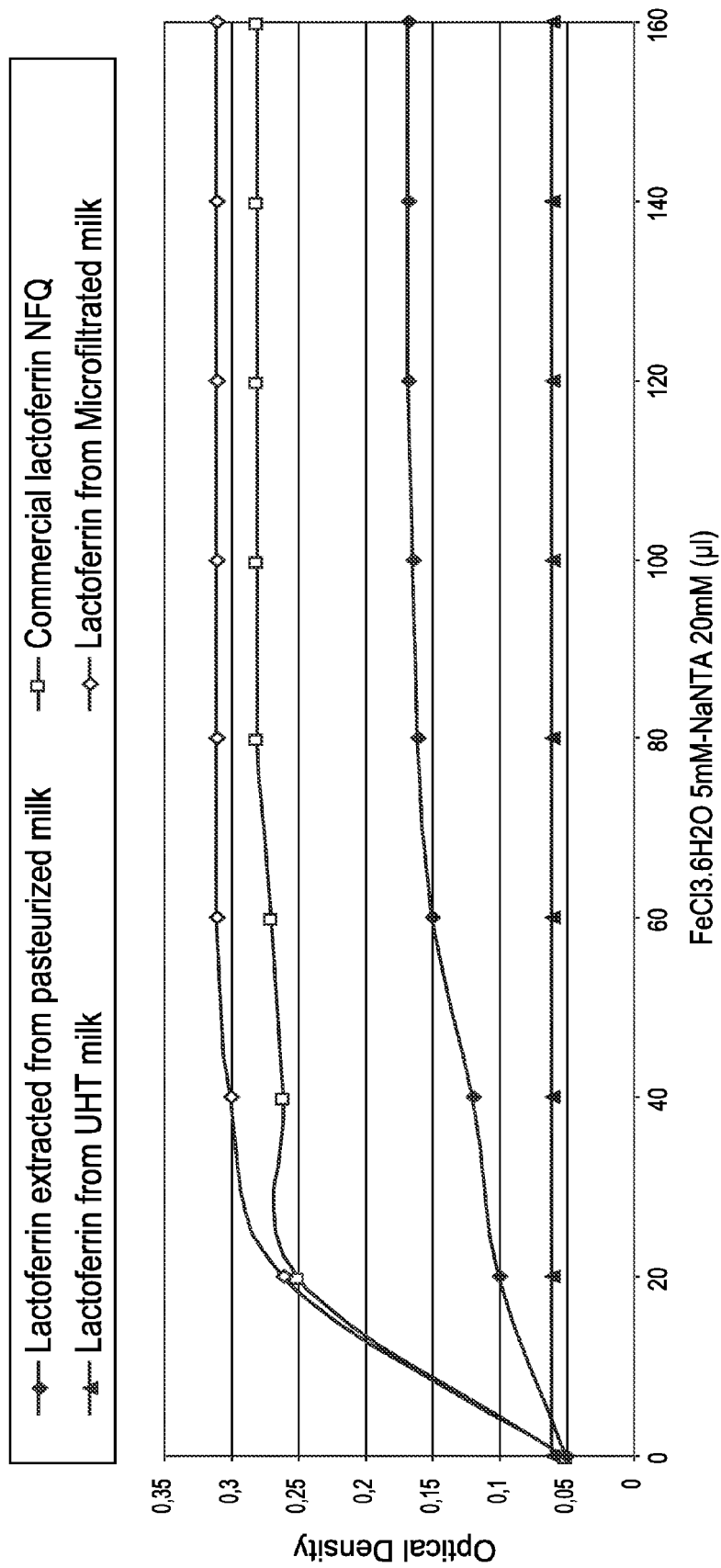
FIG. 8 illustrates the iron binding activity of lactoferrin extracted from pasteurize milk, lactoferrin from UHT milk, lactoferrin from microfiltrated milk and lactoferrin of the invention (Lf-NFQ).

When the lactoferrin is intact and active, its capacity to bind iron is maintained. On the other hand, when the protein is denatured due to a UHT treatment or partially lost due to the pasteurization treatment, it lost its iron binding capacity (FIG. 8).

The bovine lactoferrin has an iron saturation level between 9 to 20%. The results has shown that the capacity of iron is similar between a lactoferrin extracted from microfiltrated milk and the lactoferrin of the invention The difference between the two results is non significative.

Antibacterial Activity

As above explained the antimicrobial activity functionality is dependent on its protein conformation, metal binding and medium conditions (Naidu et al., 1995). Antimicrobial activity is enhanced when Lf binds to the microbial cell surface (Naidu et al., 1993). The high affinity interaction of Lf with pore-forming outer membrane proteins of gram-negative enteric bacteria, including *Escherichia coli*, is critical for the antimicrobial outcome of Lf (Ellison et al., 1988).

Thus, it is important that when we produce Lf from bovine milk or cheese whey that we are sure that there are no more bacterial lipopolysaccharides bound on the Lf structure.

Figure 9:
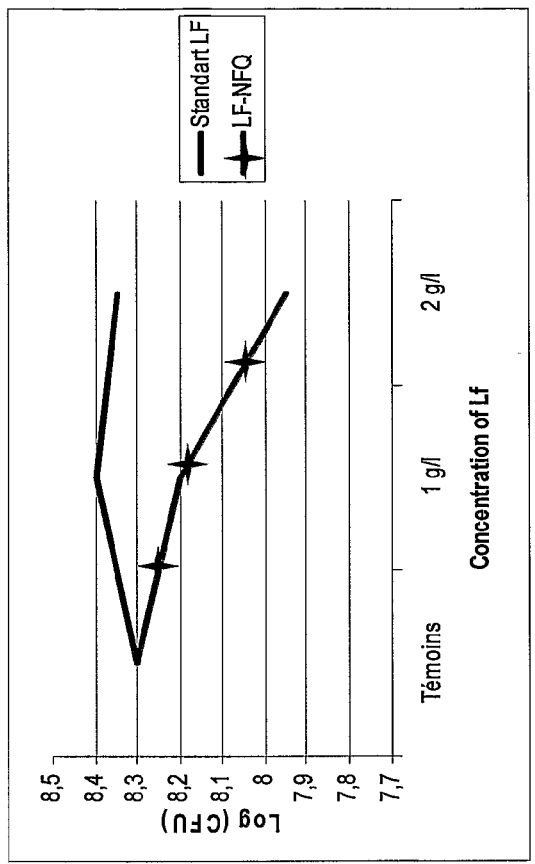
FIG. 9 illustrates the antibacterial activity. The presence of LPS on Lf structure (Lf) decreases its antibacterial activity on *Escherichia coli* compared to a free-LPS Lf (Lf-NFQ).
Figure 9:
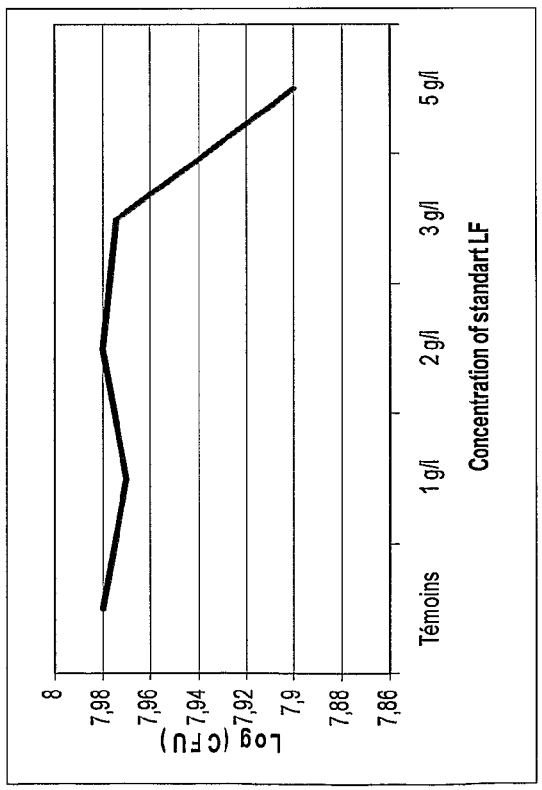
Figure 10:
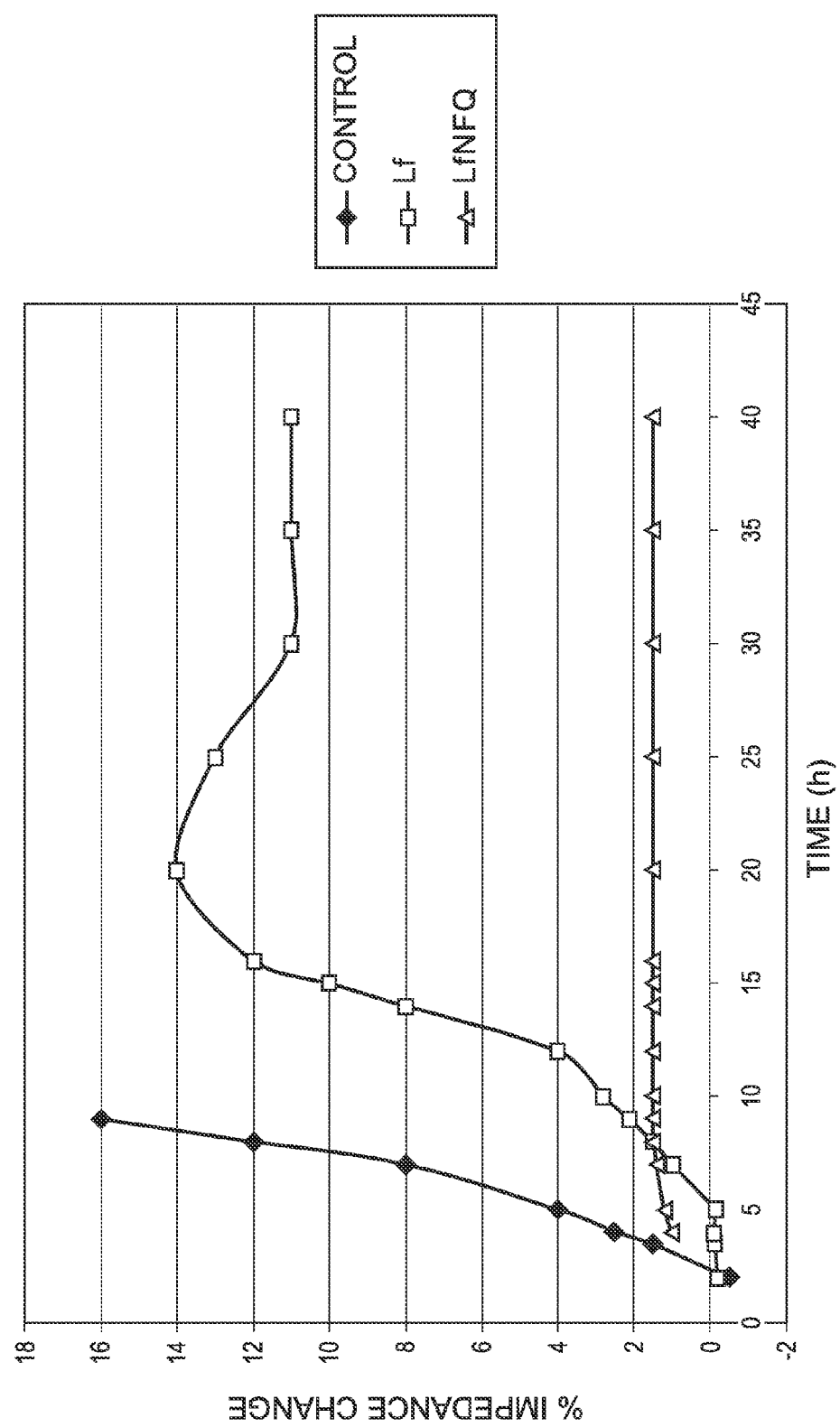
FIG. 10 illustrates the antibacterial activity. The presence of LPS on the Lf structure (Lf) decreased its antibacterial activity against *Helicobacter pylori* compared to a free-LPS Lf (Lf-NFQ)

Lactoferrin was tested towards two microorganisms *Escherichia coli* and *Helicobacter pylori*, the results are given on FIGS. 9 and 10 respectively.

*Escherichia coli* Procedure
Biological Material
E. coli K99 from BCCM/LMG bacteria Collection: laboratorium van Microbiology Universiteit Gent K. L. Ledeanckstraat 35B, 9000 Gent Selective medium SCC Coli/Coliform chromogen-agar Peptone water
Distillated water
Lots of lactoferrin
Preparation of the Bacterial Solution
Put in solution the freeze dried strains with 0.5 ml pertone
Spray 100 µl of the solution
Replicate
In the same time, to take 100 µl to put in 9 ml peptone
Make 3 tubes and incubate during 24 hours at 37° C.
Take 1 ml of the bacterial solution to take the OD
Make the OD of the bacterial solution to reach a concentration of $10^4$ to $10^5$ CFU/ml
Preparations of the Lf Solutions
Take 500 mgr of each lot of Lf
Add 100 ml of distillated water
Solution of 50 mg/ml
Filtration of the solutions
In each tube of peptone water (9 ml) take off 400 µl to reach a volume of 8.6 ml and add 0.4 ml to reach 2 mgr/ml for each Lf powder to analyse
Add 1 ml of the bacterial solution $10^5$ to $10^6$ CFU/ml
For the tube control, take 0.0 ml of peptone solution and add 1 ml of the bacterial solution.
Manipulation
Make differention solutions: $10^{-1,-2,-3,-4,-5,-6,-7}$
Culture of the Petri Dishes
Place 100 µl of the different diluted solutions in the middle of the Petri dish
Let the Petri dish at 37° C. during 24 hours.
Lecture
After 24 hours, we assess the CFU of *E. coli*.
*Helicobacter pylori* procedure
Biological Material
*Helicobacter pylori* strain: LMG 8775:3 frozen BCCM™ culture to be ordered in BCCM/LMG bacteria Colleciton: laboratorium van Microbiology Universiteit Gent K.L. Lededanckstraat 35B, 9000 Gent Tryptone Soya Agar medium with sheep blood in Petri dish
Peptone water
Distillated water
Lots of lactoferrin
Preparation of the Bacterial Solution
Put in solution the freeze dried strains with 0.5 ml peptone
Spray 100 µl of the solution
Replicate
In the same line, to take 100 µl to put in 9 ml peptone
Make 3 tubes and incubate during 2 days under anaerobiose conditions
Take 1 ml of the bacterial solution to take the OD
Make the OD of the bacterial solution to reach a concentration of $10^5$ to $10^6$ CFU/ml
Preparations of the Lf Solutions
Take 500 mgr of each lot of Lf
Add 10 ml of distillated water
Solutions of 50 mg/ml
Filtration of the solutions
In each tube of peptone water (9 ml) take off 400 µl to reach a volume of 8.6 ml and add 0.4 ml to reach 2 mgr/ml for each Lf powder to analyse
Add 1 ml of the bacterial solution $10^5$ to $10^6$ CFU/ml
For the tube control, take 9.0 ml of peptone solution and add 1 ml of the bacterial solution.
Manipulation
Make different dilutions: $10^{-1,-2,-3,-4,-5,-6,-7}$
Culture of the Petri Dishes
Place 100 µl of the different diluted solutions in the middle of the Petri dish
Let the Petri dish at 37° C. during 2 days under a anerobiose condition
Lecture
After 2 days, we assess the CFU of H.P.
Prebiotic Proliferation and Intestinal Health There are 2 possibilities:
Growth impedance detection assay and the Micro-scale optical density assay
 1) Growth Impedance Detection Assay
 A bactometer microbial Monitoring system is used to monitor the growth of probiotic either *Lactobacillus* or *Bifidus* strains by measuring impedance signals (a function of capacitance and conductance) in the cultivation media.
 A volume of 0.25 mlof Lf-NFQ followed by 0.25 ml of bacterial suspension (104 cells/ml) prepared in 0.9% saline was added to the wells. Addition of 0.5 ml bacterial suspension serves as control. The inoculated modules were incubated at 32° C. and impedance changes in the media was monitoring continuously by the Bactometer at 6 minute intervals for 48 hours. bacterial growth curves were graphically displayed as percent changes of impedance signals versus incubation time. The amount of time required to cause a series of significant deviation from the baseline impedance value was defined as the detection time. If this detection time is lower than the control, the test samples was considered to elicit "prebiotic effect".
 2) Micro-Scale Optical Density Assay
 This method to measure microbial growth in vitro is based on the turbidimetric assay. Briefly, 0.1 ml of sterile of the medium is added in the well. A 0.05 ml volume of test solution is added to designated wells followed by inoculation with 0.05 ml microbial cell suspension containing +:–$10^5$ cells/ml (diluted from an O.D. of 1 at 660 nm=109 cells/ml). After inoculation the wells are incubated at 37° C. and the microbial growth is monitored at different times as turbidity changes in culture media by measuring O.D at 660 nm using a microplate reader. Wells containing broth without microbial inoculums serve as the sterility control. Wells containing broth medium inoculated with bacteria, but without test compound served as positive growth control. The prebiotic effect is when an agent has enhanced the microbial proliferation compared to the growth control.

The free-LPS lactoferrin should shortened by 30% the detection time compared to the control. Normally, the detection time for probiotic is estimated to 15 h, the free-LPS lactoferrin should shortened by 4-5 h this detection time. Moreover, the multiplication of probiotic test strains is enhanced by >100% with free-LPS lactoferrin, which is at least twice as effective as the lactoferrin covered by lipopolysaccharides To be considered as Lf-NFQ, the Lf solution should shortened by 25 to 30% the detection time compared to the control and increase at a minimum of 100% compared to the control after 48 hours of incubation.

As we have described previously, Lf elicits microbial growth-inhibition by iron-deprivation stasis mechanism. Iron is critical for many life forms including intestinal pathogens to generate ATP by cytochrome-dependent electron transport system. However, intestinal probiotic ABL ((ABL=*Acidophilus, Bifidobacterium, Lactobacillus*) are independent of cytochrome pathways for cellular energy synthesis, therefore are selectively evasive to iron-deprivation antimicrobial stasis by Lf. This prebiotic effect by Lf in the intestinal environment is a phenomenon of natural selection to enrich beneficial probiotic flora and affect competitive exclusion of harmful pathogens by bacteriostasis. It is well known that the large intestine of breast-fed infants is colonized predominantly by species of bifidobacteria, which have protective effects against enteric pathogens. The presence of LPS and endotoxin on the Lf surface will decrease this prebiotic effect of the molecule (Table 2).

TABLE 2

Table 2: Prebiotic activity: the commercial Lf extracted from whey or from milk has a lower prebiotic activity compared to the Lf-NFQ

| Prebiotic activitie | Lf-whey | Lf-milk | Lf-NFQ |
|---|---|---|---|
| *Bifidobacterium* spp (n = 2) | 124% | 141% | 213% |
| *Lactobacillus* spp (n = 8) | 97% | 145% | 200% |

"Antioxidant Activity"

Ferric reducing/antioxidant power (FRAP BENZIE I.F.F. and STRAIN J.J. in Methods in Enzymology, Vol 299, 1990, p 15) assay as described hereafter has been used to measure the antioxidant activity of the Lf-NFQ. The FRAP reagent was prepared by mixing 40 ml of 0.3M acetate buffer (pH 3.6), 4 ml of 20 mM ferric chloride, and 4 ml of 10 mM TPTZ (2,4,6-tris(2-pyridyl-s-triazine). Serial solutions (0.1 to 1.0 mM) of 6-OH-2,5,7,8,-tetramethyl chroman-2-carboxylic acid were used as FRAP standards. All reagents were brought to 37° C. prior to the assay. FRAP assay was performed in a 96-well microplate by mixing 20 µl of distilled water, 10 µl of Lf-NFQ sample, and 150 µl of FRAP reagent. In combination studies 10 µl distilled water and 20 µl of Lf-NFQ were mixed with 150 µl of FRAP reagent. After instant incubation at 37° C. for 5 min (for ascorbic acid) and for a time lapse of 5 min to 24 hours for Lf-NFQ). The absorbance of reaction mixture was measured at 593 nm. The test compounds were given antioxidant (FRAP) scores compared to the FRAP value of ascorbic acid.

Figure 11:
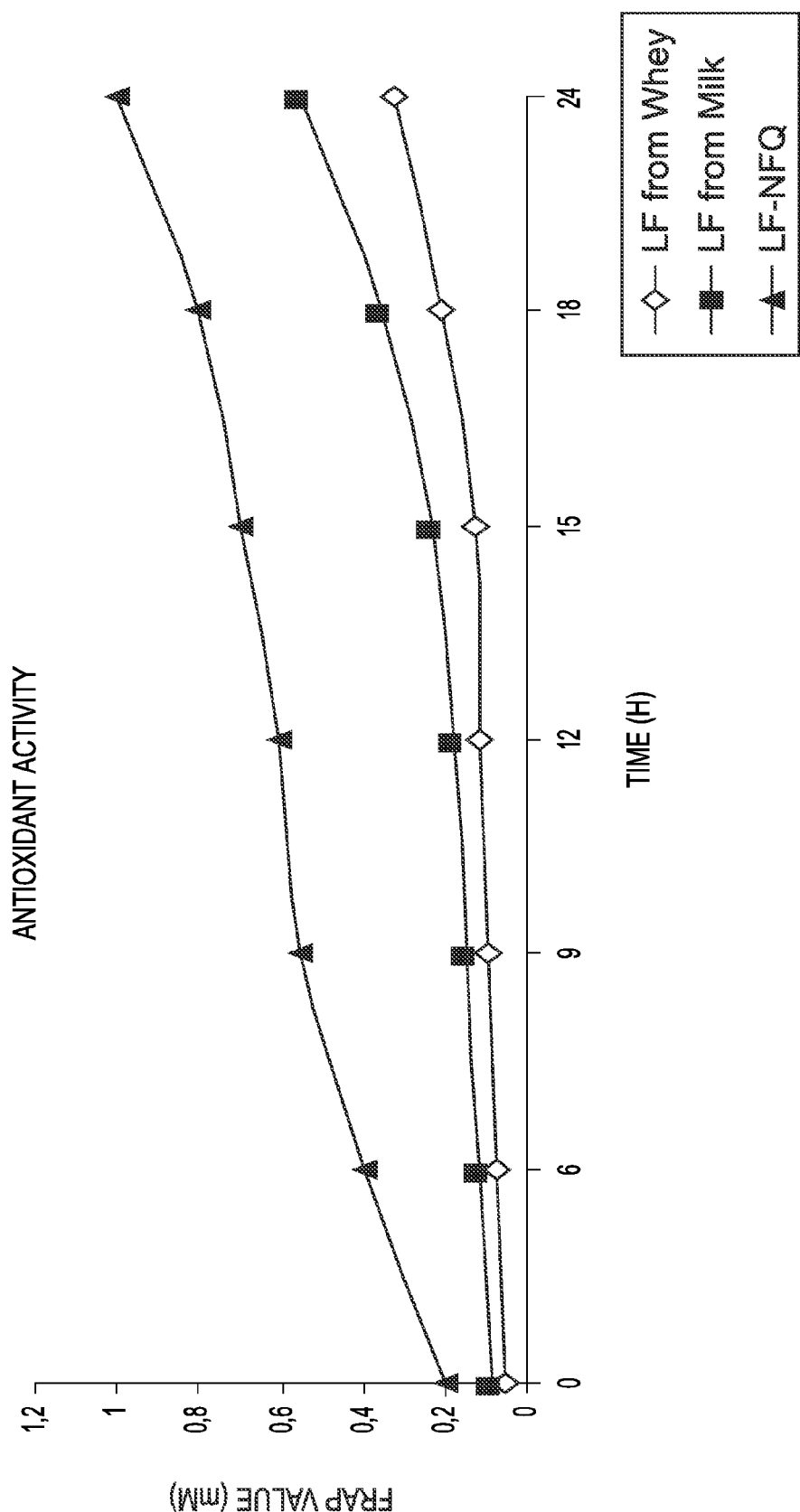
FIG. 11 illustrates the antioxidant activity of Lf-NFQ as measured by kinetic assay and compared with Lf extracted from bovine milk (12.000 pg LPS/mg Lf) and with Lf extracted from bovine whey (30.000 pg LPS/mg Lf).

A free-LPS lactoferrin (Lf-NFQ) should reach a value of 0.660 mM in 6 hours and a peak to 0.994 mM in 24 hours (FIG. 11).

A Lf can be considered as acceptable in reaching a value between 90 to 100% of this value.

Binding of bacterial lipopolysaccharides (LPS) to Lf has been implicated in the microbicidal mechanism of the protein for some gram-negative bacteria (Ellison et al., 1991). Miyazawa et his co-workers have demonstrated (1991) that the binding of LPS to lactoferrin alters the mechanism of lactoferrin binding to a myeloid cell line. Given the high likelihood that Lf would encounter considerable amounts of LPS at sites of gram-negative infections, we examined the impact of LPS binding to Lf on the ability to inhibit OH° formation resulting from iron-supplemented xanthine/xanthine oxidase system as assessed by the deoxyribose oxidation assay (Cohen et al., 1992).

The mechanism whereby LPS binding to lactoferrin decreases its priming effect on neutrophils can be assimilated to different assumptions. Possibilities include a decrease in affinity for the LPS receptor or simultaneous alteration in the signal transduction mechanism which leads to priming. Nevertheless, the data suggest the possibility that binding of LPS to lactoferrin could provide a means of decreasing the proinflammatory events which occurs in the setting of septic shock. Consistent with the possibility lactoferrin has been reported to decrease mortality in a mouse model of *E. coli*-induced septic shock (Zagulski et al., 1989). In conclusion, as we can observed in the FIG. 10, the presence of LPS on the Lf structure, limit strongly its anti-oxidant activity.

As illustrated on FIG. 11, it has been demonstrated that LPS and endotoxin free Lf (Lf-NFQ) has a superior antioxidant activity compared to its original source, the Lf-whey or Lf-milk As illustrated in the table 3, it has been demonstrated that LPS-Lf is able to induce the production of Tumor Necrosis Factor (TNF-α), Interleukin 6 (IL-6) and interleukin 8 (IL-8).

To analyze this activity of Lf, we have studied its down-regulation role on the expression of pro-inflammatory cytokines in infected with *E. coli* HB101(pRI203) and none infected intestinal epithelial cells. For this experience, we have followed the protocol described by Berlutti (Berlutti et al., 2006), using Caco-2 cells and the sample Lf-A, Lf-B, and Lf-C having 1.650 pg LP/mg Lf, 22.000 pg LPS/mg Lf and 105.000 pg/mg Lf respectively and we have compared the results with Lf-NFQ (39 pg LPS/mg Lf). When we infected the Caco-2 cells without the presence of Lf, we observe a significant increase in the expression of the pro-inflammatory cytokines such as of Il-6, Il-8 and TNF-α compared to the non-infected cells (table 3). In the presence of Lf, the expression of the cytokines is reduced in the case of Lf-NFQ but not in the case of the other Lf samples (Table 3). We can conclude that the presence of LPS on the Lf structure inhibits its activity to downregulate the expression of cytokines by infected cells. What it was surprising, was to observe that in case of non-infected cells in the presence of Lf containing a certain amount of LPS bound on its structure, the cells are able to induce the expression of cytokines and that this expression is dependent of the concentration of the LPS bound on the Lf structure, what was not the case for the Lf-NFQ having only 39 pg LPS/mg Lf (Table 3). This expression could be due to the fact that it is possible that some LPS are detached from the Lf structure due to the medium used for the cell culture and play a role as pro-inflammatory agent towards the non-infected cells. This role seems more important that the down-regulation role of the Lf.

The protocol used for such test is the following

Cell Culture

Human colon carcinoma Caco-2 cells were growth as semiconfluent monolayer in Dulbecco's modified Eagle's medium supplemented with 1.2 gr of NaHCO3/liter, 2 mmol glutamine/liter, 100 U penicillin/ml, 0.1 mg of streptomycin/ml, and 20% heat inactivated fetal calf serum in a 5% CO2 incubator at 37° C. Twelve hours before infection, monolayer were washed with PBS without Ca2+ and Mg2+ and then cultured in fresh media without fetal calf serum to avoid the presence of transferrin during infection.

Infection of Host Cells with *E. coli* HB101(pRI203)

The method has been described by Berlutti et al 2006. Semiconfluent Caco-2 cell monolayer have been infected at multiplicity of infection 100 bacteria per cell with *E. coli* HB101(pRI203) either in the absence or presence of LPS free-Lf or in the presence of Lf containing different level of LPS (100 µg protein/ml). After 4 h incubation, cells were extensively washed with PBS, without Ca2+ and Mg2+. After washing, fresh medium, containing 100 µg of gentamicin/ml, was added to monolayers infected with *E. coli* HB101 (pRI203) to kill extracellular bacteria, and cells were incubated for a further 2 h at 37° C. and washed extensively. Then the monolayers were treated with 0.3 ml trypsin-EDTA mixture (0.05% trypsin (1/250) and 0.02% EDTA) for 5 min at 37° C. and lysed by the addition of 0.5 ml of 1% deoxycholic acid. Cell lysates were diluted in PBS without Ca2+ and Mg 2+ and plated on agar with ampicillin (100 µg/ml) to quantify the number of viable intracellular *E. coli* HB101(pRI203).

Detection of IL-6, IL-8 and Tumor Necrosis Factor Alpha (TNF-α) in Caco-2 Supernatants by ELISA As described by Berlutti et al 2006, Semiconfluent Caco-2 cell monolayer were infected as described here above, either in the absence or presence of LPS free-Lf or in the presence of Lf containing different level of LPS (100 µg protein/ml). After 4 h of incubation, cells were extensively washed in PBS, monolayers were added with fresh medium containing 100 µg of gentamicin/ml, and cells were incubated for a further 24 h at 37° C. At the end, supernatants were collected for each wells, and the concentration of IL-6, IL-8 and TNF-α were determined using standard ELISA Quantikine kits (R&D Systems, Wiesbaden, Germany) and HBT kits (Holland Biotechnology BV, Firma Bierman, Bad Nauheim, Germany).

TABLE 3

Table 3: Uninfected Caco-2 cells or infected Caco-2 cells with *E. coli* HB101(pRI203) were incubated in the presence or absence of Lf-NFQ, Lf-A, Lf-B, Lf-C (100 µg/ml). the concentrations of secreted cytokines was determined by ELISA.

| Cytokines (pg/ml) | No Lf | Lf-NFQ | Lf-A | Lf-B | Lf-C |
|---|---|---|---|---|---|
| None infected Caco-2 cells | | | | | |
| TNF-α | 44 | 40 | 105 | 130 | 165 |
| IL-6 | 112 | 87 | 140 | 220 | 430 |
| IL-8 | 2700 | 2750 | 3600 | 3650 | 4600 |
| Infected Caco-2 cells with *E. coli* HB101(pRI203) | | | | | |
| TNF-α | 160 | 48 | 154 | 164 | 160 |
| IL-6 | 1200 | 150 | 1240 | 1350 | 1300 |
| IL-8 | 12250 | 3200 | 10700 | 10800 | 11500 |

P values <0.01 were considered to be significant.

Limulus Test

As we have described here above, the presence of LPS and endotoxins is considered as one of the most important contaminant for the reduction of the activity performance of the Lf. Based on the types and levels of contaminants, as well as the microbial quality assurances with a good manufacturing practice in the industrial-scale manufacturing of Lf, the purification process has been developed using a specific buffer as decontaminant agents during the different steps of the process. This technology could systematically extend the scope of treatment for contamination reduction to enhance multi-functional properties of Lf, thereby creating a powerful physiological system.

Moreover during the purification process the water which has been used to prepare all the buffers, has been distilled and treated by microfiltration, ozone (O3) and by UV 254 nm. This water was pyrogen-free.

The bioburden of different commercial Lf preparations was measured by standard assays according to the United States Food Administration (FDA) Bacteriological Analytical Manual. The LPS and endotoxin contamination in commercial Lf preparations was quantified by Limulus Amoebocyte Lysate assay using the test kit developed by Cambrex Bioscience, Walkerville, Md. The analysis of commercial Lf revealed that whey-derived Lf harbored more bioburden than milk-derived Lf. A significant portion of aerobic plate counts of whey-derived Lf were identified as Gram-positive microorganisms such as *Penicillium* spp and *Aspergillus* spp. The LPS and endotoxin levels of both commercial Lf preparations reflected their coliform and gram negative bacterial loads. The median LPS and endotoxin in whey-derived Lf were about 3 times higher than in the milk-derived Lf. The LPS and endotoxin contaminants in both Lf preparations were biologically active and induced TNF-α (Tumor Necrosis factor) production in stimulated monocytes and enterocyte cells (Caco-2 cells). (Table 3)

To avoid such problem, the quantity of LPS and endotoxins which can cover the lactoferrin structure, should be at a value between 50 to 100 pg/mgr of lactoferrin (FIG. 13) with a preference of a value <50 pg/mg Lf.

Activity on the Intestinal Cell Mucosa

Some studies have demonstrated that the Lf in laboratory is able to have an activity on the intestinal mucosa cells renewal. We have studied this activity comparing to a control, a standard commercial Lf and the Lf-NFQ when this molecule is added to special regimen to the 5 to 9 months old children who have been hospitalized due to a gastro-enteritis. The concentration of the Lf had similar to the Lf supplied by the breast milk (15 mg/kg/day). A jujenal biopsies has been performed at day 2 and day 4 after the starting of the treatment and also 5 days later. The cell renewal has been evaluated the immune-coloration technique (PCNA-cyclin immunostating—Galand et Degraef, Cell tissue Kinet, 1989, 22, 383-392). Twenty patients have received the special regimen without Lf, Seventeen patients have received the Special regimen containing the commercial Lf and eighteen patients have received the Special regimen containing the Lf-NFQ. The percentage in S-Phase mitotic cells was not significantly different in all three groups during the first 4 days of the treatment (6 to 15%).

5 days later, the percentage of cells in S-phase mitotic was significant different, we observe a rapid increasing in both Lf groups, 12 to 15% for infants who have received the Lf commercial and 18 to 21% for the infants who have received the Lf-NFQ compared to the control group where the level was 5 to 8%

Moreover, the disaccharidase activities of the brush border enterocytes increased for both Lf groups are described in the table 4 and stay low for the control group. These results suggest that Lf has a favorable action on the enterocyte renewal in phase of recovery of the acute gastro-enteritis. This action was superior in case of Lf-NFQ compared to a commercial Lf.

TABLE 4

Study: Increased enterocyte renewal during acute gastroenteritis after addition of Lf to the refeeding regimen.
Test: 17 infants-age: 5 to 10 months old-Lf commercial: 15 mg/kg/day
18 infants-age: 5 to 9 months old-Lf-NFQ: 15 mg/kg/day
Control: 20 infants-age: 5 to 15 month old-no Lf
Intestinal biopsies at day (2-4) and 5 days later

|  | Control | Lf commercial | Lf-NFQ |
|---|---|---|---|
| Enterocyte renewal (cyclin/PCNA) | | | |
| Day 2-4: S-phase mitotic cells | 6-15 | 6-15 | 6-15 |
| 5 days later: S-phase mitotic cells | 5-8 | 12-15 | 18-21 |
| Brush border dissacharidases | | | |
| Lactase: | 3-5% | 10-12% | 24% |
| Maltase | 2-6% | 19-20% | 31% |
| Sucrase | 2-4% | 10-12% | 24% |

EXAMPLE

Raw Materials

As it was explained, to avoid the denaturation of the lactoferrin and/or the destroying of its glycan chains and/or the appearance of Lf polymers by heat treatment, it is important to extract Lf from unpasteurized raw material such as skim milk before the pasteurization or free-caseinate milk, or cheese-whey or skim colostrums.

First of all, the raw material is collected at maximum 10° C. in the farms having received a control safety number from the AFSCA (Federal Agency of the Security of the Food Chain). The raw material The raw material is skimmed at 50° C. and does not need to be microfiltrated before to extract the LN containing Lf. Nevertheless, some milk cooperatives prefer to microfiltrate the raw material on 1.4μ ceramic membranes which constitute for them a replacement of the pasteurization.

Extraction of the Lactoferrin

The extraction column chromatography of which the active part which has a volume of 12 m3 contains 2.000 liters (fluidized bed) or more of extraction resin (depending of the quantity of raw material which has to be treated) The raw material is applied through this cation-exchange resin and the molecules under cationic ions from at pH 6.6 are bound on the resin, so this resin is allowed to extract the LN. The LN is a mixture mainly composed by basic proteins/enzymes. Taking into account of the color of the molecules, it is easy to observe their binding to the resin. We will observe since the beginning the changes of the resin from white to black dues to the binding of the basic molecules and mainly due to the lactoperoxidase (which is characterized by a dark green color of which the color is predominant. The flow rate can be done between 25.000 liters to 50.000 liters per hour, depending of the quality, the quantity of the raw material and its origin.

We continue to apply the raw material until that we have saturated the binding capacity of the resin (65% Lf, 30% LP and 5% contaminants) and we will observe that the color of the resin is still black. Based on the isoelectric pH of the molecules, Lf representing the highest isoelectric pH isoelectric, we can continue to apply the raw material through the column and we will observe that Lf is able to move the other molecules of the LN bound on the resin and to take their place on the resin. After a certain time corresponding to a volume 2.5 times equivalent to the volume necessary to saturated the resin, we can observe that the resin becomes red, that means that the resin has almost only Lf bound on its support. In such conditions, the lactenin will be composed of 88% Lf, 10% LP and 2% contaminants.

This LN of which the concentration of its components will be depending of the source of the raw material, of the time or of the volume which has been applied, will be eluted by the application of a 1.35 M NaCl solution (8%). The solution so collected that we called Lactenin (LN) or Milk Basic Protein (MBP), will be concentrated and diafiltratred using 30 kD membranes. Considering the time where we will start the purification process (2nd step), the MBP solution will be microfiltrated through 0.8 μm ceramic membranes.

Purification of the Lactoferrin

The LN is stocked at 4° C. before to be applied to another cation-exchange resin. The LN solution will be applied on a cationic-exchange resin. The volume which will be applied will depend of the volume of the resin in relation with the concentration of lactoferrin in the LN. This purification resin is a Sepharose Fast Flow manufactured by Amersham.

Every day a certain volume of the LN solution, depending of the volume of the purification resin will be applied of the cationic-exchange resin equilibrated with a buffer 50 mM sodium acetate pH 4 à 8.8 and a NaCl solution at a concentration from 0.02 M to 1.5 M.

The purification process will be proceeded as follows:
Impurities A: eluted using a buffer sodium acetate, pH 6.5, NaCl 0.05M
Lactoperoxidase: eluted using a buffer sodium acetate, pH 6.5, NaCl 0.3M
LPS, endotoxin, proteases and angiogenin: eluted using a buffer sodium acetate, pH 8, NaCl 0.5M
Lactoferrin: eluted using a buffer ammonium acetate, pH 8, NaCl 1M.

The Lf eluted, will be collected in a clean room, like laminar flow clean room.

Ultrafiltration—Diafiltration

The lactoferrin solution is concentrated by ultrafiltration (tangential ultrafiltration) using 30 kD organic membranes and diafiltrated to obtain a final solution of 3Ms;

Concentration

The low conductivity lactoferrin solution is concentrated afterwards to reach a concentration of 15-16%

Microfiltration

The lactoferrin is submitted to a final microfiltration using 0.22 µm membranes

Freeze-Drying

The lactoferrin solution is freeze-dried at 45° C. under vacuum

Grinding

For some applications, the lactoferrin powder is crushed and micronized to obtain a 80 mesh size powder.

Mixing

The different production of lactoferrin will be mixed to obtain a lot of 200 kgs. Samples of 50 gr and 10 gr will be realized.

Packaging

The lactoferrin powder is packed in food grade aluminium-polyethylene sachets.

All the steps where the purified lactoferrin is handled or manipulated are conducted in enclosed space environmentally controlled in order to avoid contamination of the purified lactoferrin, for example aseptic clean rooms.

The invention also concerns the use of the Lactoferrin obtained by the method as above described, to accelerate the maturation of the gastrointestinal tract in the newborn, or the tissue repair of the intestinal mucosa in conditions of the recovery of a gastroenteritis.

The invention also concerns the use of the Lactoferrin obtained by the method as above described, to increase the hepatic synthesis in the new born.

The invention also concerns the use of the Lactoferrin obtained by the method as above described, to enhance natural killer (NK) activity of monocytes and to increase both the NK and lymphokine-activated killer (LAK) cell cytoxicity functions.

The invention also concerns the use of the Lactoferrin obtained by the method as above described, as a potential anti-tumor agent through its specific receptors on macrophages, T and B-lymphocytes and leukemia cells.

The invention also concerns the use of the Lactoferrin obtained by the method as above described, to reduce expression of some pro-inflammatory cytokines.

The invention also concerns the use of the Lactoferrin obtained by the method as above described, to inhibit or to kill bacteria or to treat diseases associated to biofilm bacteria, such diseases being cystic fibrosis or oral inflammation.

The invention also concerns the use of the Lactoferrin obtained by the method as above described, to prepare wound care solutions, wounds care solutions, ear care solutions, ointments for wound healing or eye care solutions.

The invention also concerns the use of the Lactoferrin obtained by the method as above described, for the uptake of iron through the epithelial cells in case of Iron deficiency and Iron deficiency anemia patients and also for pregnant women.

The invention also concerns the use of the Lactoferrin obtained by the method as above described, to treat respiratory infectious diseases (URTI and LRTI).

The invention claimed is:

1. A method for production of Lactoferrin comprising:
   a) disposing of a raw material that has not been treated at a temperature greater than 50° C.,
   b) extracting the raw material on a cation exchange resin with an excluded solute concentration solution in order to obtain a solution of Lactenin (LN) or Milk Basic Protein (MBP), wherein the excluded solute is sodium chloride,
   c) purifying the LN or MBP solution on a cation exchange resin equilibrated with an acetate buffer at a pH between 4 and 9 by eluting with different buffer solutions containing different solute concentrations, and
   d) collecting a fraction of the solution containing the Lactoferrin, the Lactoferrin having a purity of more than 95%, having no polymers, and being substantially free of LPS, endotoxins and angiogenin.

2. The method as defined in claim 1, wherein the collecting of the Lactoferrin is conducted in a clean room.

3. The method as defined in claim 1, wherein the purifying of the LN or MBP solution on a cation exchange resin is performed in flow through or bind and elute mode.

4. The method as defined in claim 1, further comprising, after the extracting of the raw material on a cation, concentrating and diafiltrating the solution of LN or MBP.

5. The method as defined in claim 1, wherein the purifying of the LN or MBP solution on a cation exchange resin comprises at least four elutions, collecting of the contaminants, collecting of the lactoperoxidase, collecting of the LPS, endotoxins, proteases and angiogenin, and collecting of the Lactoferrin.

6. The method as defined in claim 5, wherein the collecting of the lactoperoxidase and the collecting of the LPS, endotoxins, proteases and angiogenin are performed at a pH between 4 and 7.

7. The method as defined in claim 1, wherein the collecting of the Lactoferrin is performed at a pH comprised between 7 and 9.

8. The method as defined in claim 1, wherein in the purifying of the LN or MBP solution on a cation exchange resin, the solute is sodium chloride at a concentration comprised between 0.02 to 1.5 M.

9. A method of accelerating maturation of the gastrointestinal tract in a newborn, or repairing a tissue of the intestinal mucosa of an individual suffering from a condition associated with recovery of gastroenterotitis, the method comprising:
   administering to a subject in need thereof a purified Lactoferrin extracted from milk or from whey, obtained according to the method of claim 1, having a purity of greater than 95%, containing less than 50 pg/mL of LPS, endotoxins, and angiogenin, and having an iron saturation level in a range of from 9% to 20%.

10. A method of increasing hepatic synthesis in a newborn, the method comprising:
    administering to a newborn a purified Lactoferrin extracted from milk or from whey, obtained according to the method of claim 1, having a purity of greater than 95%, containing less than 50 pg/mL of LPS, endotoxins, and angiogenin, and having an iron saturation level in a range of from 9% to 20%.

11. A method of enhancing natural killer (NK) activity of monocytes and increasing both the NK and lymphokine-activated killer (LAK) cell cytoxicity functions, the method comprising:
    administering to a subject in need thereof a purified Lactoferrin extracted from milk or from whey, obtained according to the method of claim 1, having a purity of greater than 95%, containing less than 50 pg/mL of LPS, endotoxins, and angiogenin, and having an iron saturation level in a range of from 9% to 20%.

12. A method for preparing an antitumor agent, the method comprising utilizing a purified Lactoferrin extracted from milk or from whey, obtained according to the method of claim 1, having a purity of greater than 95%, containing less than 50 pg/mL of LPS, endotoxins, and angiogenin, and having an iron saturation level in a range of from 9% to 20%, and that acts through its specific receptors on macrophages, T and B-lymphocytes and leukemia cells.

13. A method of reducing expression of some pro-inflammatory cytokines, the method comprising:
   administering to a subject in need thereof a purified Lactoferrin extracted from milk or from whey, obtained according to the method of claim 1, having a purity of greater than 95%, containing less than 50 pg/mL of LPS, endotoxins, and angiogenin, and having an iron saturation level in a range of from 9% to 20%.

14. A method of inhibiting or killing bacteria or treating diseases associated to biofilm bacteria, the method comprising:
   administering a purified Lactoferrin extracted from milk or from whey, obtained according to the method of claim 1, having a purity of greater than 95%, containing less than 50 pg/mL of LPS, endotoxins, and angiogenin, and having an iron saturation level in a range of from 9% to 20%.

15. The method as defined in claim 14, wherein the diseases associated to biofilm bacteria are cystic fibrosis or oral inflammation.

16. A method of preparing wound care solutions, ear care solutions, ointments for wound healing or eye care solutions, the method comprising:
   utilizing a purified Lactoferrin extracted from milk or from whey, obtained according to the method of claim 1, having a purity of greater than 95%, containing less than 50 pg/mL of LPS, endotoxins, and angiogenin, and having an iron saturation level in a range of from 9% to 20%.

17. A method of causing uptake of iron through epithelial cells, the method comprising:
   administering to a subject in need thereof a purified Lactoferrin extracted from milk or from whey, obtained according to the method of claim 1, having a purity of greater than 95%, containing less than 50 pg/mL of LPS, endotoxins, and angiogenin, and having an iron saturation level in a range of from 9% to 20%.

18. A method of treating respiratory infectious diseases (URTI and LRTI), the method comprising:
   administering to a subject in need thereof a purified Lactoferrin extracted from milk or from whey, obtained according to the method of claim 1, having a purity of greater than 95%, containing less than 50 pg/mL of LPS, endotoxins, and angiogenin, and having an iron saturation level in a range of from 9% to 20%.

19. Purified bovine Lactoferrin, extracted from bovine milk or from whey, obtained according to the method of claim 1, having a purity of greater than 95%, containing less than 50 pg/mL of LPS, endotoxins, and angiogenin, and having an iron saturation level in a range of from 9% to 20%.

* * * * *